United States Patent [19]
Turi et al.

[11] Patent Number: 5,567,376
[45] Date of Patent: Oct. 22, 1996

[54] METHOD OF FORMING TEXTILE-LIKE APERTURED PLASTIC FILMS

[75] Inventors: Mordechai Turi, Princeton Junction; Edmund Z. DeRossett, Mercerville; Ching-Yun M. Yang, Princeton Junction, all of N.J.

[73] Assignee: Chicopee, New Brunswick, N.J.

[21] Appl. No.: 417,404

[22] Filed: Apr. 5, 1995

Related U.S. Application Data

[63] Continuation of Ser. No. 4,379, Jan. 14, 1993, abandoned, which is a continuation of Ser. No. 744,744, Aug. 14, 1991, abandoned.

[51] Int. Cl.⁶ ............................................ B29C 59/00
[52] U.S. Cl. .................. 264/455; 264/504; 425/290; 425/387.1
[58] Field of Search ........................... 83/30, 53, 177; 264/504, 156, 455; 425/387.1, 290

[56] References Cited

U.S. PATENT DOCUMENTS

| | | |
|---|---|---|
| 2,862,251 | 12/1958 | Kalwaites . |
| 2,987,240 | 6/1961 | Boyer et al. . |
| 3,485,706 | 12/1969 | Evans . |
| 3,485,708 | 12/1969 | Ballon et al. . |
| 3,498,874 | 3/1970 | Evans et al. . |
| 3,746,607 | 7/1973 | Harmon et al. . |
| 3,929,135 | 12/1975 | Thompson et al. . |
| 3,989,867 | 11/1976 | Sisson . |
| 4,133,310 | 8/1979 | Lloyd et al. . |
| 4,135,021 | 1/1979 | Patchell et al. . |
| 4,262,049 | 4/1981 | Kaspar . |
| 4,324,246 | 4/1982 | Mullane et al. . |
| 4,342,314 | 8/1982 | Radel et al. . |
| 4,463,045 | 7/1984 | Ahr et al. . |
| 4,539,256 | 9/1985 | Shipman . |
| 4,552,708 | 11/1985 | Koger, II et al. . |
| 4,609,518 | 9/1986 | Curro et al. . |
| 4,629,457 | 12/1986 | Ness . |
| 4,629,643 | 12/1986 | Curro . |
| 4,637,819 | 1/1987 | Ouellette . |
| 4,695,334 | 9/1987 | Mays . |
| 4,695,422 | 9/1987 | Curro et al. . |
| 4,726,989 | 2/1988 | Mrozinski . |
| 4,753,843 | 4/1988 | Noda . |
| 4,835,042 | 5/1989 | Dohzoho . |
| 4,839,216 | 6/1989 | Curro et al. . |
| 4,859,519 | 8/1989 | Cabe, Jr. et al. . |
| 4,867,881 | 9/1989 | Kinzer . |
| 4,950,264 | 8/1990 | Osborn, III . |
| 5,006,394 | 4/1991 | Baird . |
| 5,009,653 | 4/1991 | Osborn, III . |
| 5,023,130 | 6/1991 | Simpson et al. . |
| 5,078,710 | 1/1992 | Suda . |
| 5,098,764 | 3/1992 | Drelich et al. . |
| 5,158,819 | 10/1992 | Goodman et al. . |
| 5,244,711 | 9/1993 | Drelich et al. . |
| 5,268,218 | 12/1993 | Zafiroglu . |
| 5,281,461 | 1/1994 | Greenway et al. . |
| 5,288,536 | 2/1994 | Zafiroglu . |
| 5,368,909 | 11/1994 | Langdon et al. . |
| 5,368,910 | 11/1994 | Langdon et al. . |
| 5,368,926 | 11/1994 | Thompson et al. . |

FOREIGN PATENT DOCUMENTS

| | | |
|---|---|---|
| 0156471 | 10/1985 | European Pat. Off. . |
| 304617 | 9/1989 | European Pat. Off. . |

*Primary Examiner*—Catherine Timm

[57] ABSTRACT

Apertured plastic films comprise a stretchable thermoplastic polymeric material having a plurality of micro-holes defined by a network of fiber-like elements. The films are produced by directing fluids, especially water, against the upper surface of a starting film in the form of columnar streams in a contact zone, while the film is supported on a backing element. The films of the invention are useful as covering materials for absorbent products such as diapers, wound dressings and sanitary napkins.

14 Claims, 18 Drawing Sheets

FIG. 2
FIG. 3
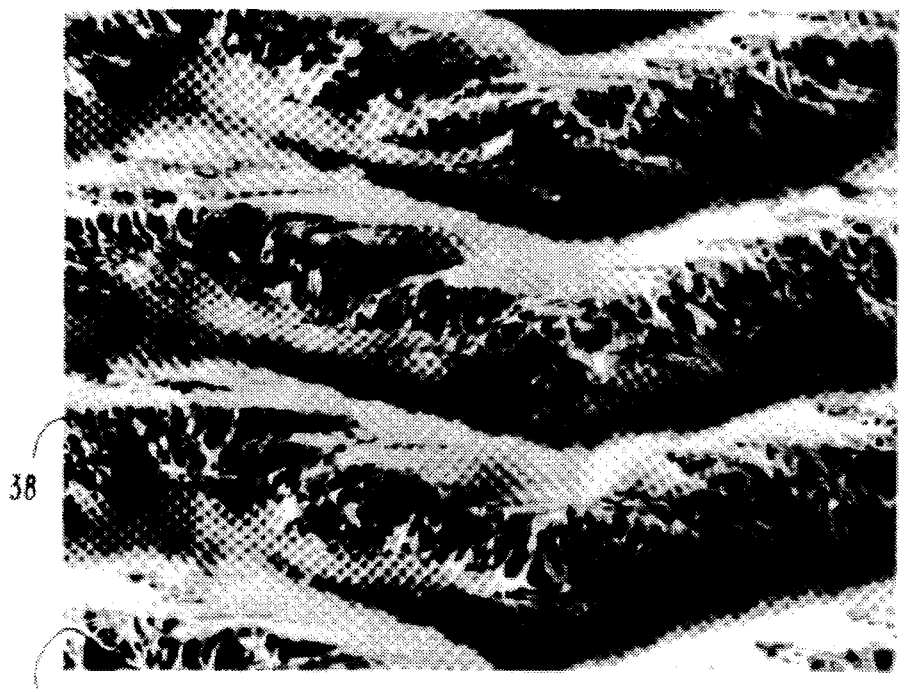

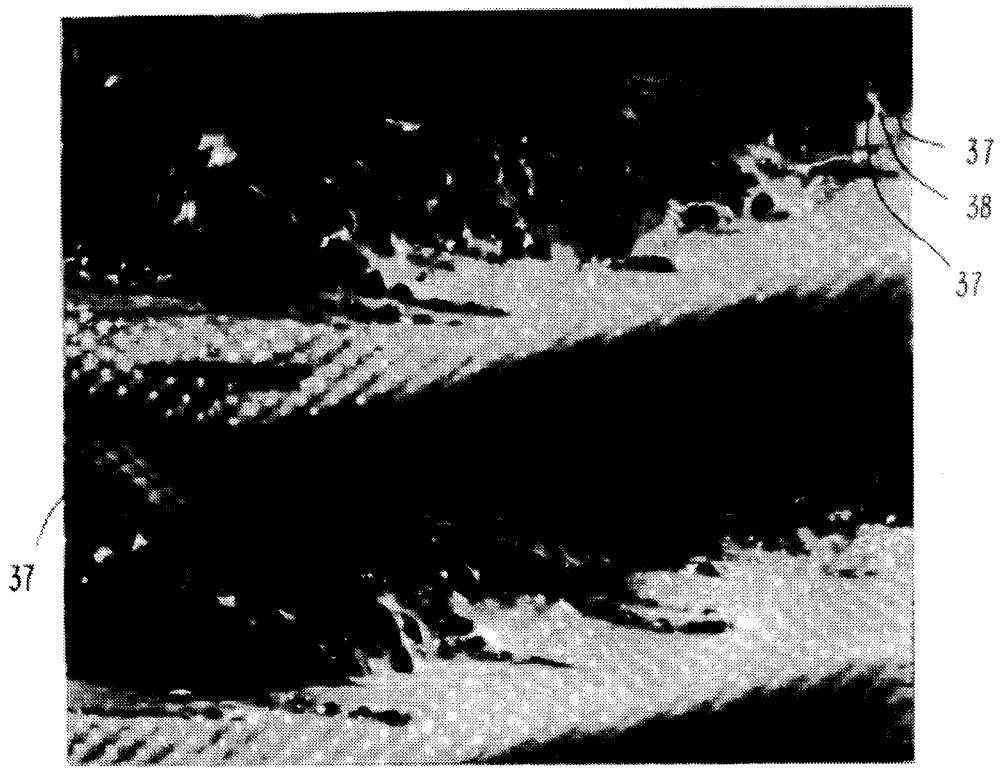
FIG. 4
FIG. 5
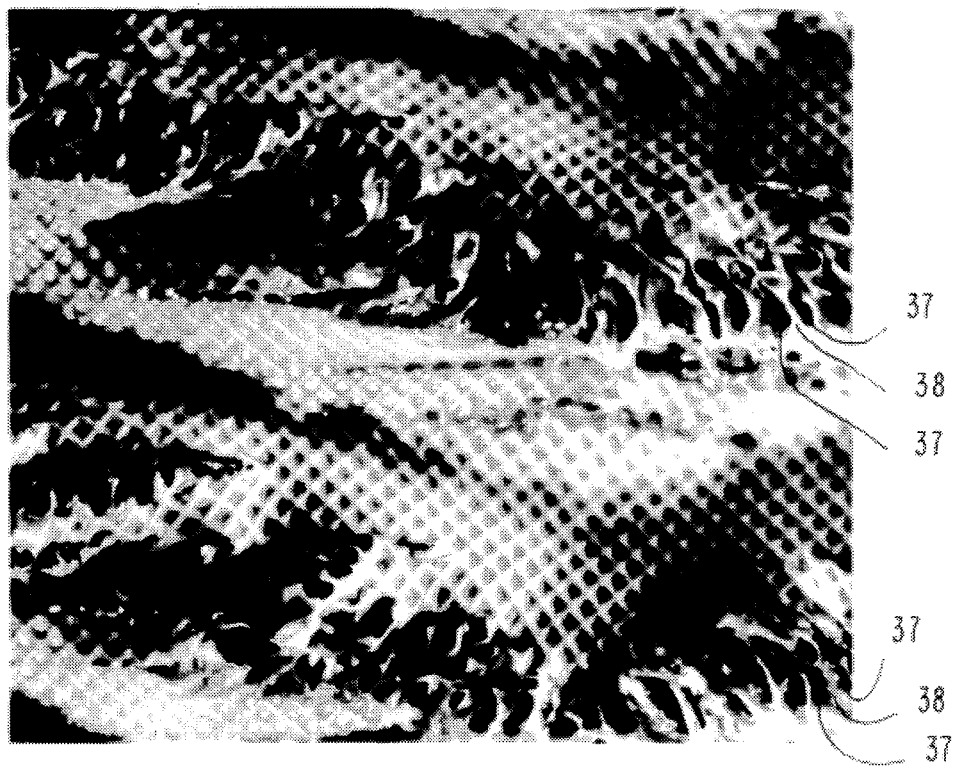

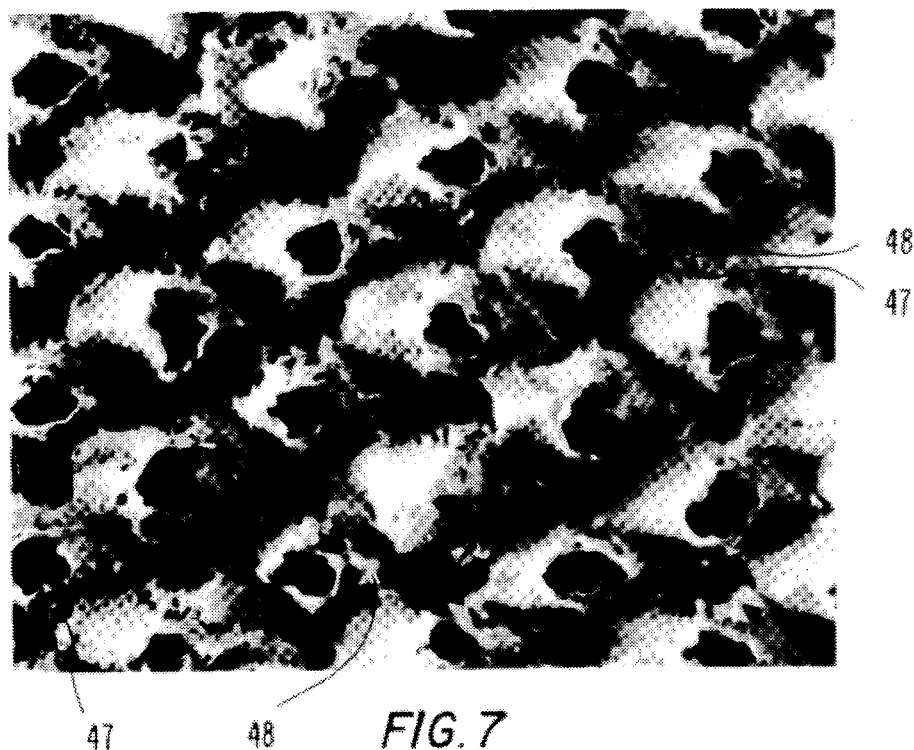
FIG. 7
FIG. 8
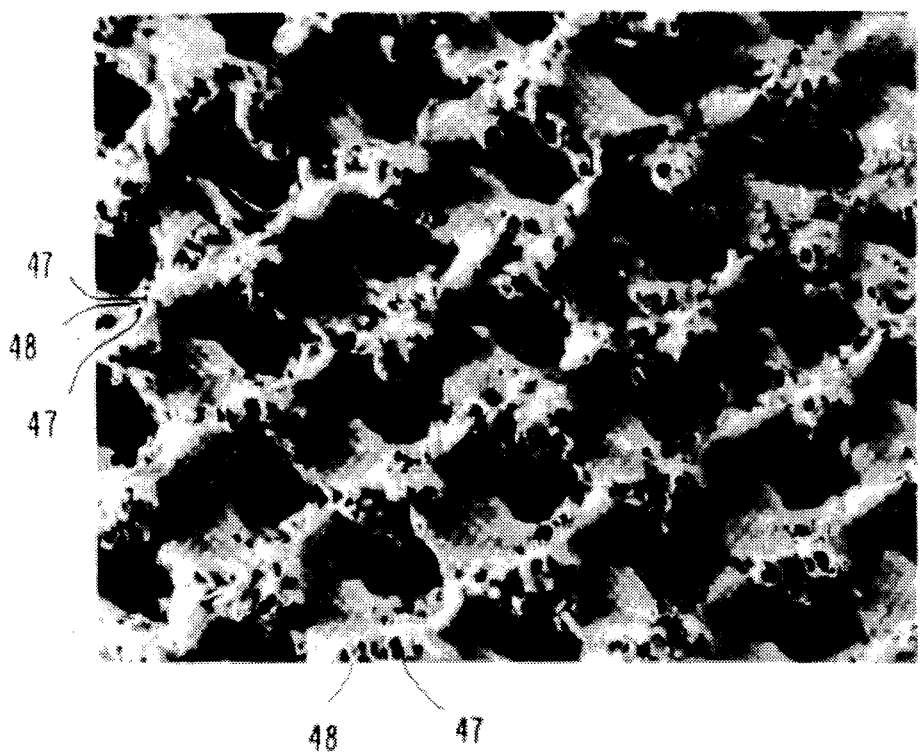

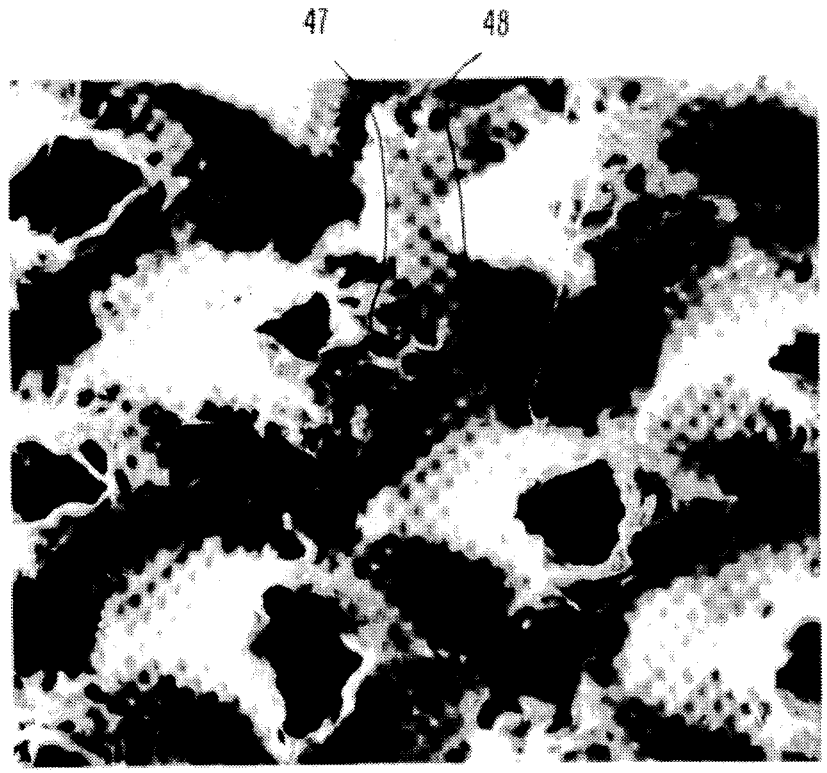
FIG. 9
FIG. 10
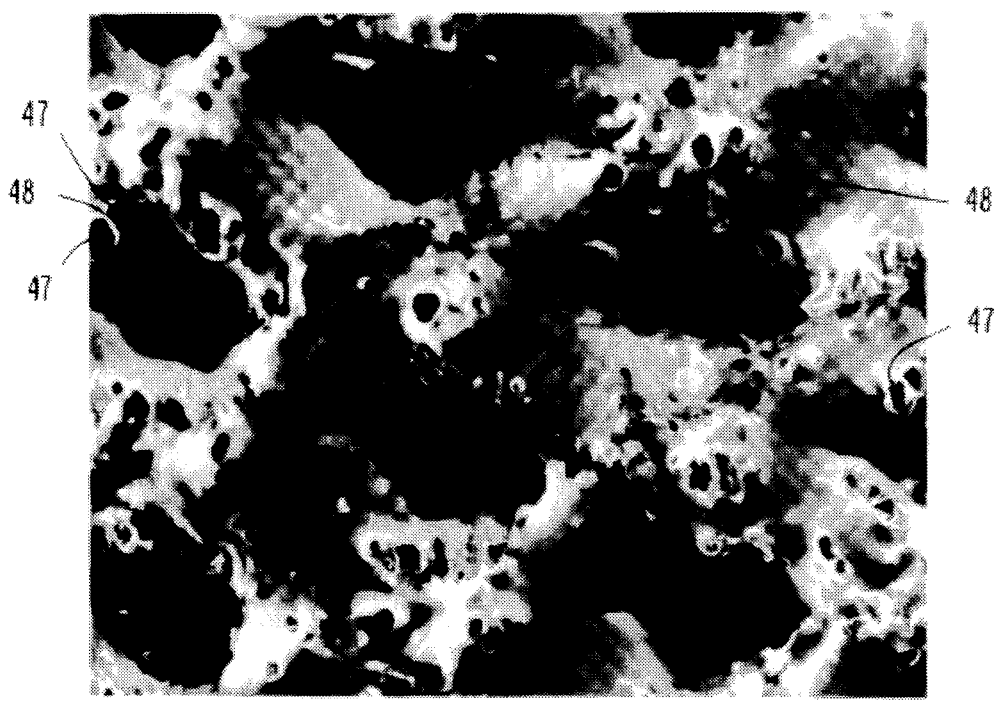

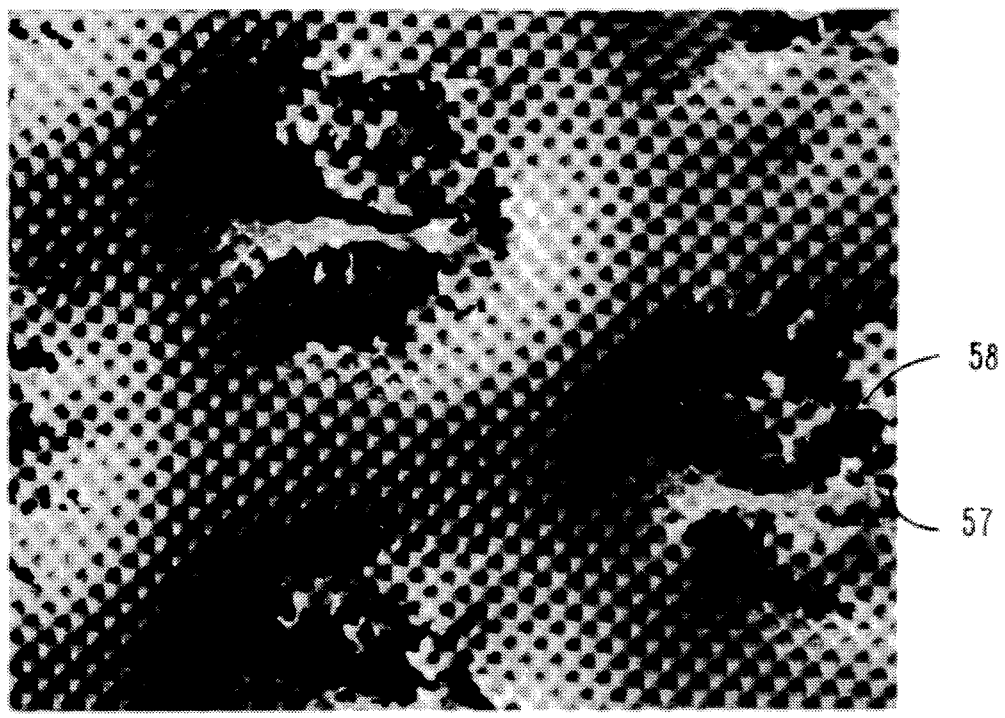
FIG. 14
FIG. 15
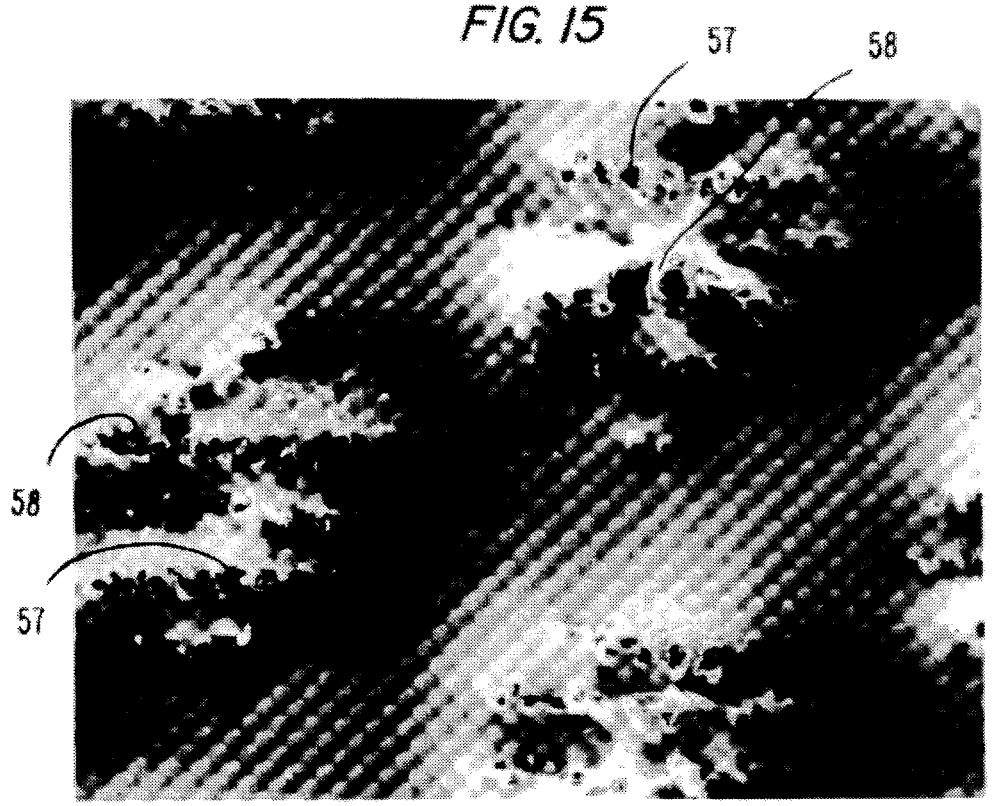

METHOD OF FORMING TEXTILE-LIKE APERTURED PLASTIC FILMS

This is a continuation of U.S. patent application Ser. No. 08/004,379, filed Jan. 14, 1993, abandoned, which is a continuation of U.S. patent application Ser. No. 07/744,744, filed Aug. 14, 1991, abandoned, which applications are hereby incorporated by reference.

FIELD OF THE INVENTION

The present invention relates generally to apertured films and more particularly to apertured plastic films comprising a plurality of micro-holes defined by a network of fiber-like elements or micro-strips of drawn plastic material. The invention also relates to methods and apparatus for making such apertured films and to products comprising such apertured films.

BACKGROUND OF THE INVENTION

Nonwoven fabrics have been used for a wide variety of applications for at least fifty years. Nonwoven fabrics are textile-like materials produced directly from a web of fibers so as to eliminate the many time consuming steps involved in converting staple length fibers into woven or knitted goods. In one method of making a nonwoven fabric, a web of fibers is produced, e.g. by carding or air laying techniques, and the fibrous web is then strengthened by the application thereto of a polymeric binding agent. In another method of making a nonwoven, the fibrous web is subjected to fluid forces which serve to entangle the fibers, thus providing strength to the finished material. Nonwoven fabrics are inherently porous structures, i.e. they comprise openings or pores allowing for the passage of fluids such as air and water or aqueous solutions. In addition, nonwoven fabrics may be tailored so as to have good softness, drapeability, and tactile impression. Owing to their desirable characteristics, nonwovens have been employed as facing materials for absorbent products such as disposable diapers, sanitary napkins, incontinent devices, wound dressings and the like.

More recently, efforts have been made to produce porous or liquid-permeable facing materials for absorbent products by using plastic films as the starting materials. For example, it is known to produce an apertured plastic film by placing a heated thermoplastic sheet material on a patterned perforated surface and applying a vacuum thereto. The vacuum pulls the softened sheet material through the perforations, thereby causing the film to rupture and form apertures.

U.S. Pat. No. 3,929,135 to Thompson et al discloses perforated topsheet materials for absorptive devices such as sanitary napkins, incontinent pads, bandages and the like. These topsheet materials are constructed from liquid impervious materials such as low density polyethylene and comprise a plurality of tapered capillaries each of which has a base opening in the plane of the top sheet and an apex opening which is remote from the plane of the top sheet. The tapered capillaries disclosed by Thompson et al. are preferably provided in the form of a frustum of a conical surface and have an angle of taper of from about 10° to 60°.

U.S. Pat. No. 4,324,276 to Mullane discloses an apertured formed film having a caliper of less than about 0.030 inch (0.075 cm), an open area of at least 35% and a plurality of apertures at least 75% of which have an equivalent hydraulic diameter (EHD) of at least 0.025 inch (0.064 cm). The apertured formed film disclosed by Mullane et al. is useful as a topsheet for disposable absorbent products of the type mentioned above.

U.S. Pat. No. 4,839,216 to Curro et al. discloses a debossed and perforated plastic material produced by providing a starting film on a perforated forming surface and applying an unconstrained liquid stream to the upper surface of the starting film. The liquid stream has sufficient force and mass flux to cause the film to be deformed toward the forming surface, such that the material acquires a substantial three-dimensional conformation, and to cause perforations to be created therein.

European Patent Application 0 304 617 in the name of Kao Corporation discloses a covering sheet for a sanitary article. The covering sheet comprises an opaque, hydrophobic film having land portions and recesses, said recesses being formed to have a bottom portion and side walls. The side walls have a slanting part which is provided with an opening such that the slanting part is not covered by the land portion. This patent states that the opening is always exposed to sight when it is looked down at.

U.S. Pat. No. 4,690,679 discloses an apertured film comprising a first layer of a first polymeric film and a second layer of a second polymeric film. Apertured films wherein the apertures have average equivalent circular diameters ranging from about 0.010 inches (0.0254 cm) to about 0.030 inches (0.0762 cm) are disclosed as being useful as covering materials for absorbent products.

Other patents relating to apertured films and methods and apparatus for making the same include U.S. Pat. No. 3,632,269 to Doviak et al. and U.S. Pat. No. 4,381,326 to Kelley.

SUMMARY OF THE INVENTION

In accordance with one aspect of the present invention, there are provided apertured films which have the porosity, open area, softness, strength, hand, textile-like appearance, tactile impression, conformability and draping properties characteristic of many nonwoven fabrics made from fibrous webs, and which do not have the undesirable characteristics, such as stiffness, non-conformability and "plastic feel" often encountered in apertured plastic films of the prior art.

Apertured plastic films of the present invention comprise a plurality of micro-holes defined by a network of fiber-like elements or micro-strips of drawn plastic material. The micro-holes are for the most part irregular in shape, that is, they do not assume a clearly identifiable geometric configuration such as circular, square or oval. The micro-holes may be provided in a discontinuous pattern of distinct groups or clusters. The pattern of distinct groups or clusters of micro-holes may be either random or regular; in either instance the micro-holes in each distinct group or cluster may be randomly distributed therein. Furthermore, the micro-holes are non-uniform in size and have small equivalent hydraulic diameters (EHD).

The individual fiber-like elements in the network of fiber-like elements comprise drawn portions of the starting plastic film. These fiber-like elements, sometimes also referred to herein as "fibrils", cooperate with the above-mentioned micro-holes to provide the apertured film of the invention with a visual appearance reminiscent of nonwoven fabrics made from air-laid or carded webs of staple-length fibers or spun-bonded nonwovens. The fiber-like elements also provide the apertured films of the invention with good softness and drapeability. The fiber-like elements or fibrils have lengths ranging from about 0.005 inch (0.013 cm) to about 0.05 inch (0.127 cm); widths ranging from about 0.001 inch (0.003 cm) to about 0.035 inch (0.089 cm); and thicknesses ranging from about 0.00025 inch (0.0006 cm) to about 0.002 inch (0.005 cm).

Apertured films according to the present invention may have low open areas, ranging from about 1% to 15%. Such low open areas are advantageous in instances where the apertured film of the invention is used as a cover material for the absorbent core of products such as sanitary napkins and disposable diapers. In such cases, the low open area substantially reduces the tendency of fluids (e.g. menstrual fluid or urine) absorbed by the absorbent core to travel back through the apertured film to rewet its upper surface and contact the skin of the wearer. At the same time, the apertured films of the present invention, when suitably pigmented, e.g. with titanium dioxide, are very effective in masking stains on the surface of the absorbent core as a result of having been contacted by body exudates such as menstrual fluid and urine.

In certain embodiments, the apertured film of the invention further includes a plurality of secondary openings whose area is substantially larger than the area of the aforementioned micro-holes. It will be understood that the percent open area of the apertured film may be varied over a wide range by varying the number and/or size of the micro-holes and/or the secondary openings.

The apertured films of the present inventions are produced by directing controlled fluid forces against one surface of a relatively thin, stretchable plastic film while the film is supported on its other surface by a backing member. Backing members suitable for use in the practice of the present invention comprise localized support regions for supporting the film; recessed zones into which the film may be deformed by the application of the fluid forces thereto; and means for moving the applied fluid away from the backing member.

In one specific method for producing apertured films in accordance with the present invention, the backing member includes a plurality of spaced-apart, upwardly extending pyramids arranged in a predetermined pattern on one surface of the backing member. The pyramids have bases which are four-sided and the pyramids are oriented so that the side edges defining the base of the pyramids are disposed at an angle of about 60° with respect to the side edges of the backing member (said side edges of the backing member corresponding and being parallel to the machine direction of the film as it is disposed on said backing member). The plurality of pyramids in said specific pattern are arranged in rows running crosswise of the backing member and in columns running lengthwise of the backing member, with the pyramids in any given row being staggered or offset with respect to the pyramids in each of the two rows immediately adjacent said given row. The side walls of the plurality of pyramids define a first set of valleys and a second set of valleys, with each set of valleys running at an angle to the machine direction of the backing member. The two sets of valleys mutually intersect each other. The valleys in each set of valleys are arranged in parallel relationship with each other. The backing member under discussion further comprises a plurality of circular openings for removal of the applied fluid. The openings are located in the aforementioned valleys between the pyramids.

In another specific method for producing apertured film in accordance with the present invention, the backing member for supporting the plastic film comprises a base portion and a plurality of continuous, upwardly extending, spaced-apart, arcuate ribs disposed in parallel relationship with respect to one another. The arcuate ribs, as seen in top plan view, are in the form of a sine-like wave. The backing member further comprises a plurality of valleys or depressed regions defined by adjacent pairs of arcuate ribs. A plurality of apertures are located in the depressed regions and run through the backing member from one major surface to the other.

In yet another specific method for producing apertured film in accordance with the present invention, the backing member comprises a base portion with a plurality of apertures running through the thickness thereof. In this embodiment of the backing member, which may be provided in flat plate or cylindrical form (as may the aforementioned backing members) there are no upstanding elements such as the aforementioned pyramids or sinusoidal-like ribs.

BRIEF DESCRIPTION OF THE DRAWINGS

The present invention will be more clearly understood by reference to the accompanying detailed description and the appended drawings in which:

FIG. 2 is a photomicrograph of the upper surface of the apertured film illustrated schematically in FIG. 1 enlarged about 20 times;

FIG. 3 is a photomicrograph of the lower surface of the apertured film illustrated schematically in FIG. 1 enlarged about 20 times;

FIG. 4 is a photomicrograph of the upper surface of the apertured film illustrated schematically in FIG. 1 enlarged about 40 times;

FIG. 5 is a photomicrograph of the lower surface of the apertured film illustrated schematically in FIG. 1 enlarged about 40 times;

FIG. 7 is a photomicrograph of the upper surface of the apertured film illustrated schematically in FIG. 6 enlarged about 20 times;

FIG. 8 is a photomicrograph of the lower surface of the apertured film illustrated schematically in FIG. 6 enlarged about 20 times;

FIG. 9 is a photomicrograph of the upper surface of the apertured film illustrated schematically in FIG. 6 enlarged about 40 times;

FIG. 10 is a photomicrograph of the lower surface of the apertured film illustrated schematically in FIG. 6 enlarged about 40 times;

FIG. 14 is a photomicrograph of the upper surface of the apertured film illustrated schematically in FIG. 11 enlarged about 40 times;

FIG. 15 is a photomicrograph of the lower surface of the apertured film illustrated schematically in FIG. 11 enlarged about 40 times;

DESCRIPTION OF THE PREFERRED EMBODIMENTS

Figure 1:
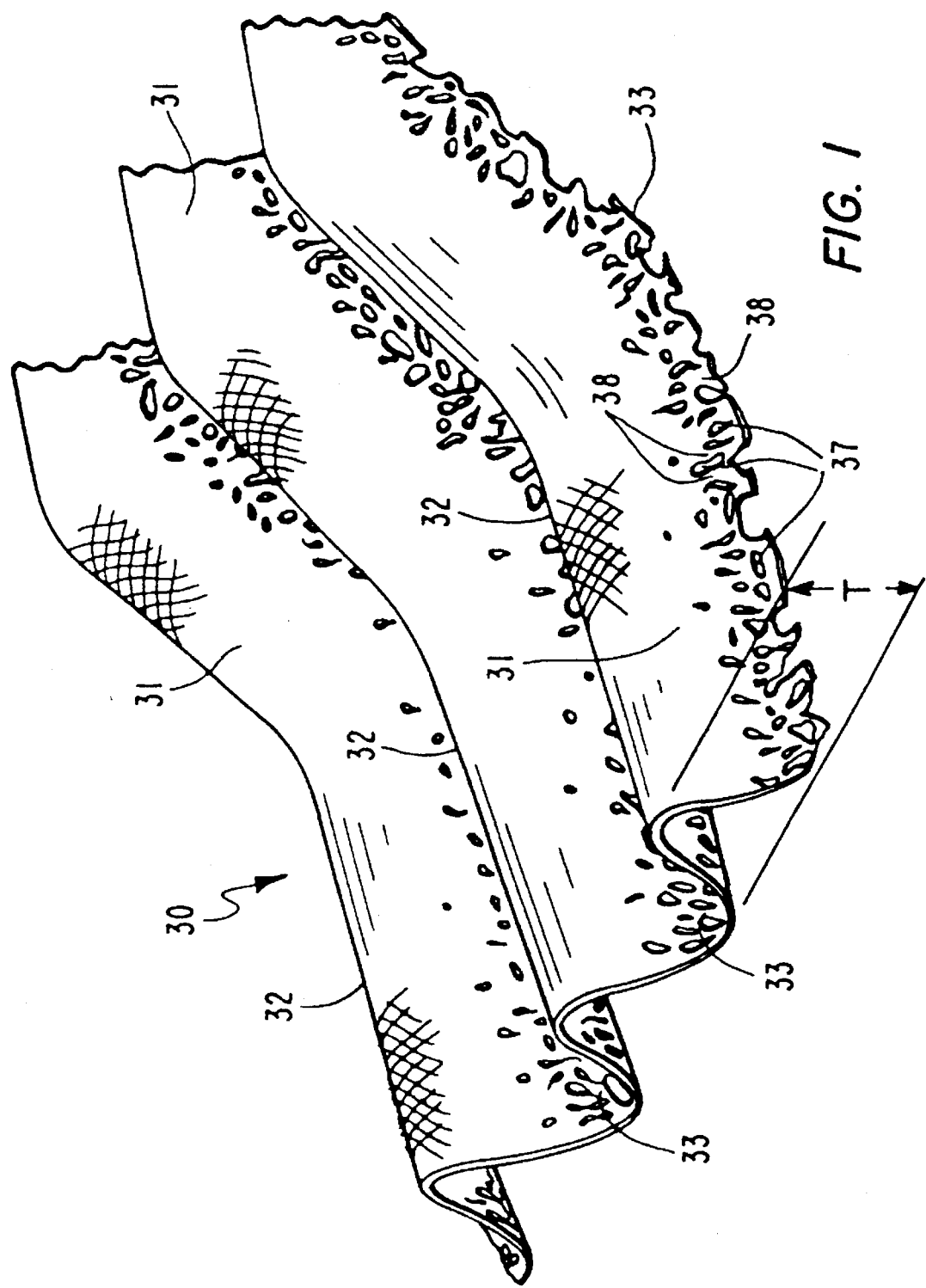
FIG. 1 is a schematic perspective view of the upper surface of one embodiment of an apertured plastic film according to the present invention.

Referring now to FIGS. 1–5 of the drawings, there is shown one embodiment of an apertured plastic film in accordance with the present invention. Apertured plastic film 30 is made from a thin layer of embossed, stretchable thermoplastic polymeric material which, prior to processing, has a thickness which may conveniently range from about 0.0005 inch (0.0013 cm) to about 0.005 inch (0.0127 cm). Apertured plastic film 30 comprises angled, generally vertically oriented side walls 31 which meet on the upper surface of the film to form a series of generally parallel ridges 32. The angled side walls define a series of generally parallel valleys 33. As seen in plan view, both the ridges and the valleys have an arcuate, sinusoidal-like configuration. The valleys 33 and the lower reaches of side walls 31 adjacent those valleys comprise a multiplicity of micro-holes 37 defined by a network of very fine fiber-like elements 38. The bulk or thickness, T, of apertured film 30, i.e. the vertical distance from a valley 33 to a ridge 32 is approximately 20 mils (0.05 cm).

Turning to FIGS. 6–10 of the drawings, there is shown a second embodiment of an apertured plastic film in accordance with the present invention. Apertured film 40 is also made from a layer of embossed, stretchable, thermoplastic polymeric material whose thickness, prior to processing, is in the range of from about 0.0013 cm to about 0.0127 cm. Apertured film 40 comprises a plurality of generally vertically extending cone-like structures 41 whose sloping side walls 41a define valleys 43 therebetween. The valleys 43 and adjacent portions of the side walls of the cone-like structures comprise a large plurality of micro-holes 47 defined by a network of very fine fiber-like elements 48. Cone-like structures 41 comprise secondary openings 42 whose areas are substantially larger than the areas of micro-holes 47. The bulk or thickness, T, of the apertured plastic film, i.e. the perpendicular distance from a valley 43 to the top of cone-like structure 41 is approximately 25 mils (0.064 cm).

A third embodiment of an apertured plastic film in accordance with the present invention is illustrated in FIGS. 11–15 of the drawings. Apertured plastic film 50 comprises a thin layer of stretchable thermoplastic film comprising a plurality of micro-holes 57 which are provided or arranged in a plurality of groups or clusters 55 of micro-holes arranged in a regular pattern. Each cluster 55 comprises a plurality of rows 56 of micro-holes, five such rows being illustrated in FIG. 11. There are a large number of randomly distributed micro-holes 57 in each row 56, with these micro-holes being separated from one another in the rows by very fine, fiber-like elements 58. Adjacent rows 56 of micro-holes 57 are separated from one another in the clusters 55 by strips 59 of unapertured material. As illustrated, the regions 52 around and between neighboring clusters 57 are substantially free of micro-holes 57.

The thickness, T, of an apertured film of the invention is larger than the thickness, t, of the starting film from which it was derived. For example, the observed thickness, T, of the apertured film of FIGS. 1–5 is about 0.05 cm; and the thickness, T, of the apertured film of FIGS. 6–10 is about 0.064 cm.

The depth of valleys 33 is not uniform throughout the apertured film. Valleys 33 may vary somewhat in depth in going from one region of the apertured film to another. For example, the depth of a valley at the lower left-hand portion of FIG. 1 may be less than, the same as, or greater than the depth of that same valley at the upper right-hand portion of FIG. 1.

Figure 16:
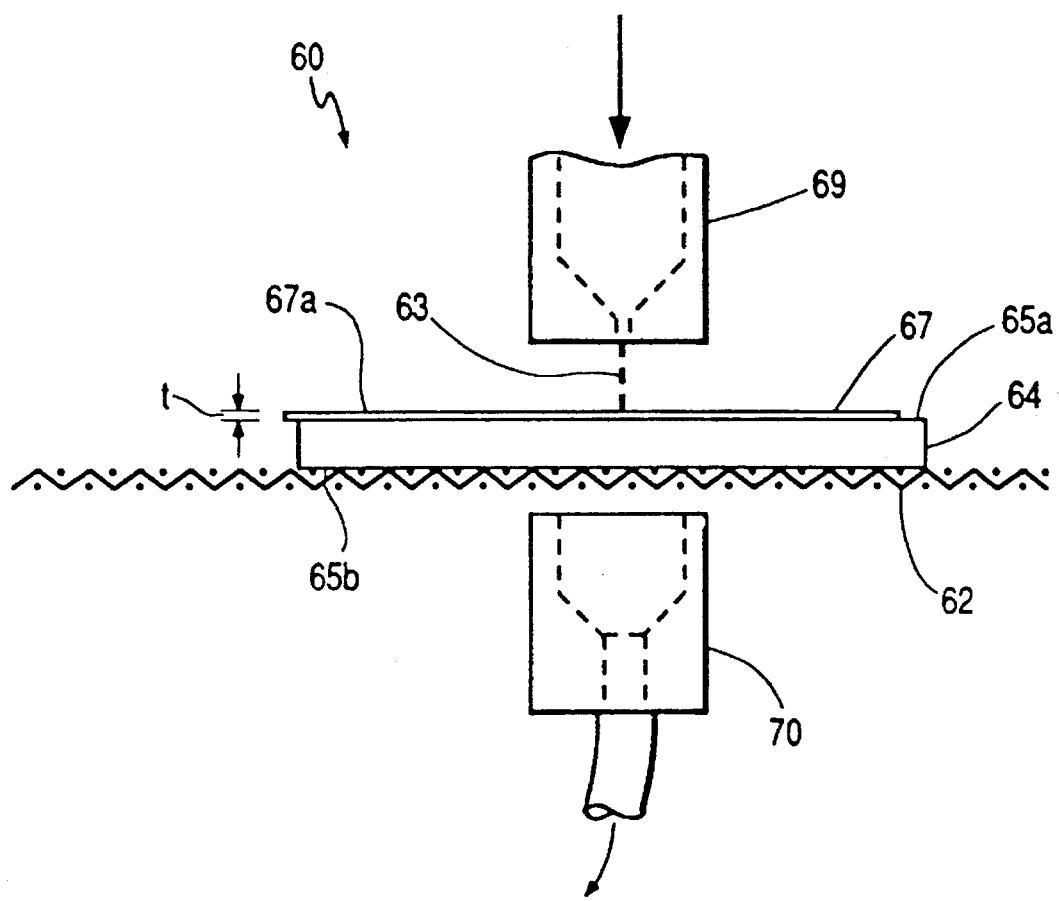
FIG. 16 is a schematic view of apparatus for producing apertured films according to the present invention.

FIG. 16 is a schematic view showing an apparatus for making apertured plastic films of the present invention. Apparatus 60 comprises a movable conveyor belt 62 and, placed on top of this belt, to move with the belt, a backing member 64. The backing member has a plurality of openings (not shown in FIG. 16) disposed therein, said openings running through the thickness of the backing member from its upper surface 65a to its lower surface 65b.

Placed on top of the backing member is a thin, continuous, uninterrupted film 67 of thermoplastic polymeric material. This film may be vapor permeable or vapor impermeable; it may be embossed or unembossed; it may, if desired, be corona-discharge treated on one or both of its major surfaces or it may be free of such corona discharge treatment. The stretchable film may comprise any thermoplastic polymeric material including, by way of example, polyolefins, such as polyethylene (high, linear low or low density) and polypropylene; copolymers of olefins and vinyl monomers, such as copolymers of ethylene and vinyl acetate or vinyl chloride; polyamides; polyesters; polyvinyl alcohol and copolymers of olefins and acrylate monomers such as copolymers of ethylene and ethyl acrylate. Film comprising mixtures of two or more such polymeric materials may also be used. The machine direction (MD) and cross direction (CD) elongation of the starting film to be apertured should be at least 100% as determined according to ASTM Test No. D-882 as performed on a Instron test machine run at a jaw speed of 50 inches/minute (127 cm/minute). The thickness of the starting film (i.e. the film to be apertured) is preferably uniform and may range from about 0.0005 inch (0.0013 cm) to about 0.005 inch (0.0127 cm); preferably, the starting film has a thickness, t, between 0.0005 inch (0.0013 cm) and 0.003 inch (0.0076 cm). Co-extruded films can be used as can films which have been modified, e.g. by treatment with a surface active agent. The starting film can be made by any known technique such as casting, extrusion or blowing.

Situated above starting film 67 is a manifold 69 for applying a fluid 63, preferably water, to the upper surface 67a of the starting film as said film, supported on backing member 64, is moved with conveyor belt 62. The water may be applied at varying pressures. Disposed beneath the conveyor belt is a vacuum manifold 70 for removing water which is directed onto upper surface 67a of starting film 67 as it passes under manifold 69.

In operation, starting film 67 is placed on backing member 64 and the film and backing member are passed back and forth under manifold 69 a number of times until the desired apertured film is produced.

Manifold 69 comprises a plurality of holes which may range in number from about 30 per lineal inch to about 100 per lineal inch. Preferably, the number of holes in the manifold ranges from about 35 per lineal inch to about 50 per lineal inch. The holes are preferably circular in configuration and have diameters ranging from about 0.003 inch (0.0076 cm) to about 0.01 inch (0.0254 cm), preferably 0.005 inch (0.0127 cm) to 0.007 inch (0.018 cm). After the starting film and backing member are passed under manifold 69 a number of times, the application of the water is stopped and the application of vacuum is continued to assist in dewatering the resulting apertured film of the invention. The apertured film is removed from the backing member and dried by any convenient technique such as the application thereto of a warm air flow or by solvent extraction.

Figure 17:
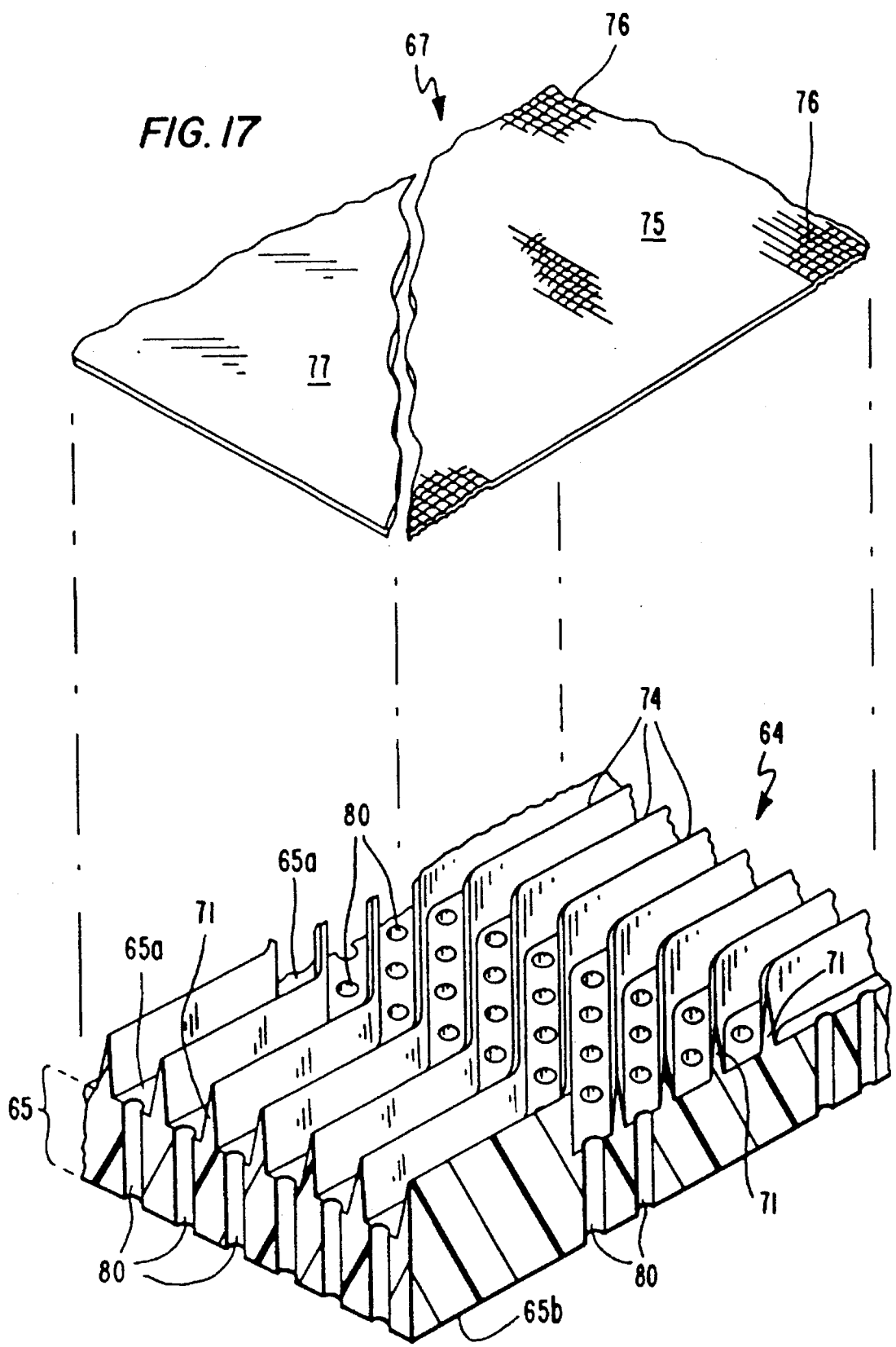
FIG. 17 is an exploded perspective view of a starting plastic film and a backing member on which the starting film is positioned for processing in accordance with the present invention.

FIG. 17 is an exploded perspective view of certain parts, i.e. starting film 67 and backing member 64, described earlier herein in conjunction with FIG. 16. As mentioned earlier, starting film 67 comprises a thermoplastic polymeric material or mixture of two or more such polymeric materials and, as illustrated in FIG. 17, the film may be embossed or unembossed. A portion 75 of starting film 67 comprising embossments 76, and a portion 77 of unembossed film 67 are shown in the upper portion of FIG. 17.

Figure 18:
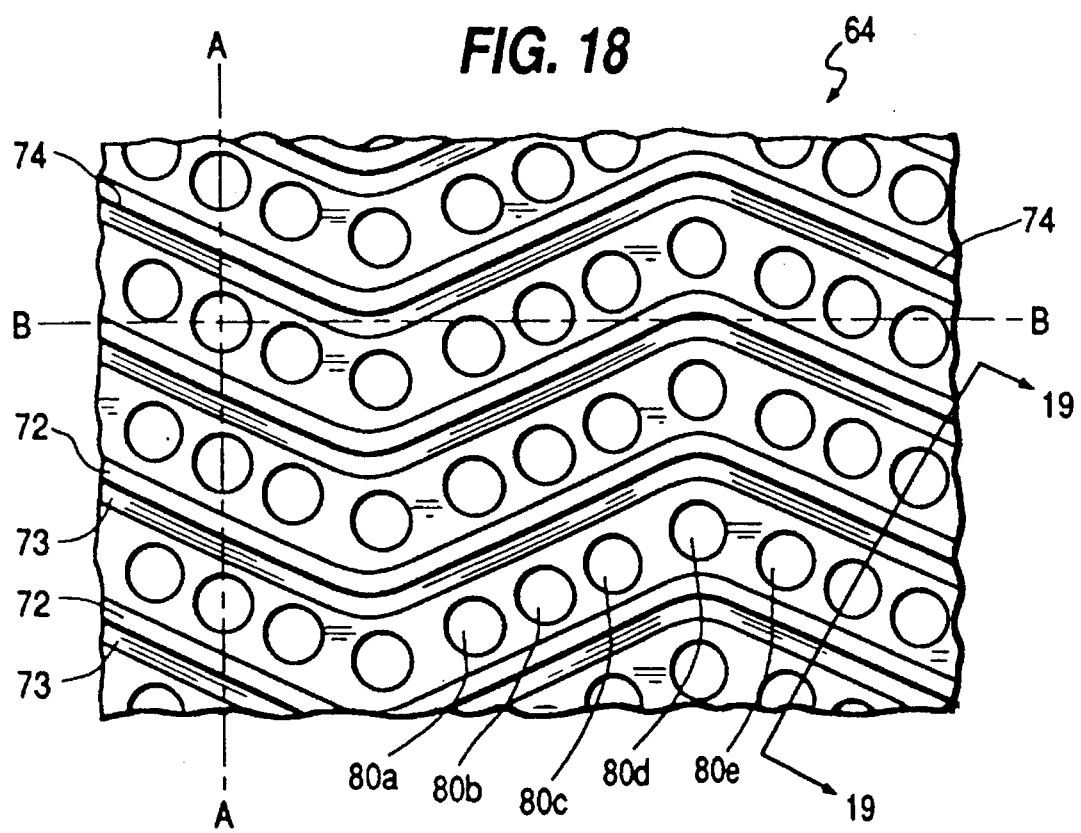
FIG. 18 is a top plan view of the backing member shown in the lower portion of FIG. 17.

Backing member 64 comprises base portion 65 having an upper surface 65a and a lower surface 65b. Backing member 64 further comprises a plurality of apertures 80 running through the thickness of base 65 from upper surface 65a to lower surface 65b. As will be seen hereinafter, apertures 80 are provided to allow for removal of water during the manufacture of apertured film according to the invention. Backing member 64 also includes a plurality of vertically-extending support elements 71. These support elements comprise a base 78 coinciding with the plane of upper surface 65a of portion 65 and a pair of angled side walls 72,73 (best seen in FIGS. 18 and 19). Side walls 72,73 extend upwardly from base 78 to meet at a land portion or ridge 74. Support elements 71 are aligned in parallel and spaced equidistantly from one another. They may run either parallel to, perpendicular to, or at any angle to the sides of the backing member. As shown in FIGS. 17 and 18, support elements 71, when viewed in plan, are generally sinusoidal-like or wavy in configuration. It will be understood that the support elements may be provided in other configurations, e.g. straight-line, zig-zag and the like.

Figure 20:
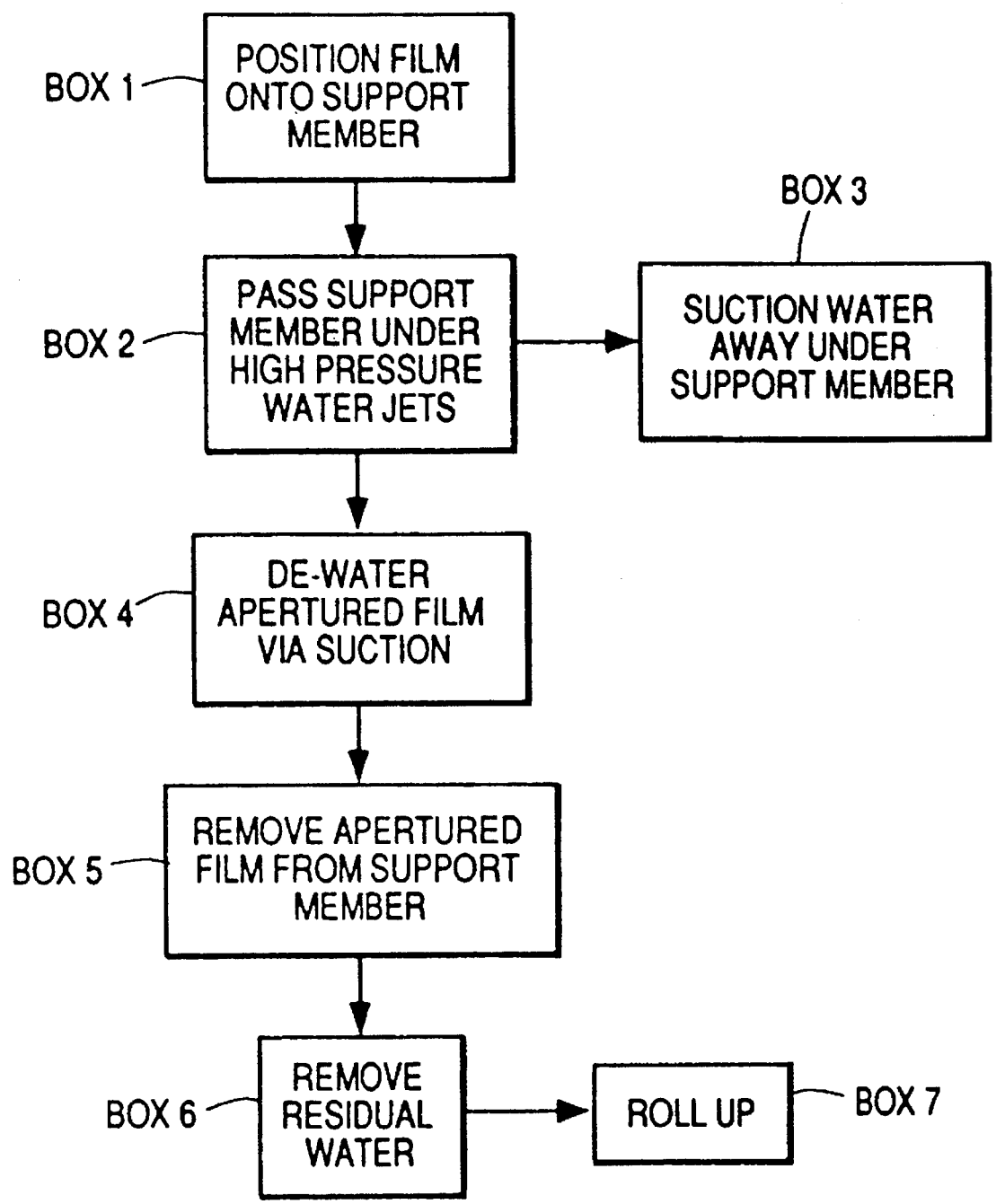
FIG. 20 is a block diagram showing the various steps of the process for producing apertured film according to the present invention.

FIG. 20 is a block diagram showing the several steps in the process for producing the novel apertured films of the present invention. The first step in the process is to position a piece of thin, stretchable film of thermoplastic polymer material on a support member (Box 1). The support member with the stretchable film thereon is passed under high pressure fluid ejecting nozzles (Box 2). The preferred fluid is water. The water is transported away from the support member, preferably using a vacuum (Box 3). The film is de-watered, suction being preferred for this purpose (Box 4). The de-watered apertured film is removed from the support member (Box 5). Residual water is removed from the apertured film, e.g. by applying a stream of air thereto (Box 6). The apertured film is then rolled up to await use as is or as a structural component of another product such as a sanitary napkin, disposable diaper or wound dressing (Box 7).

Figure 21:
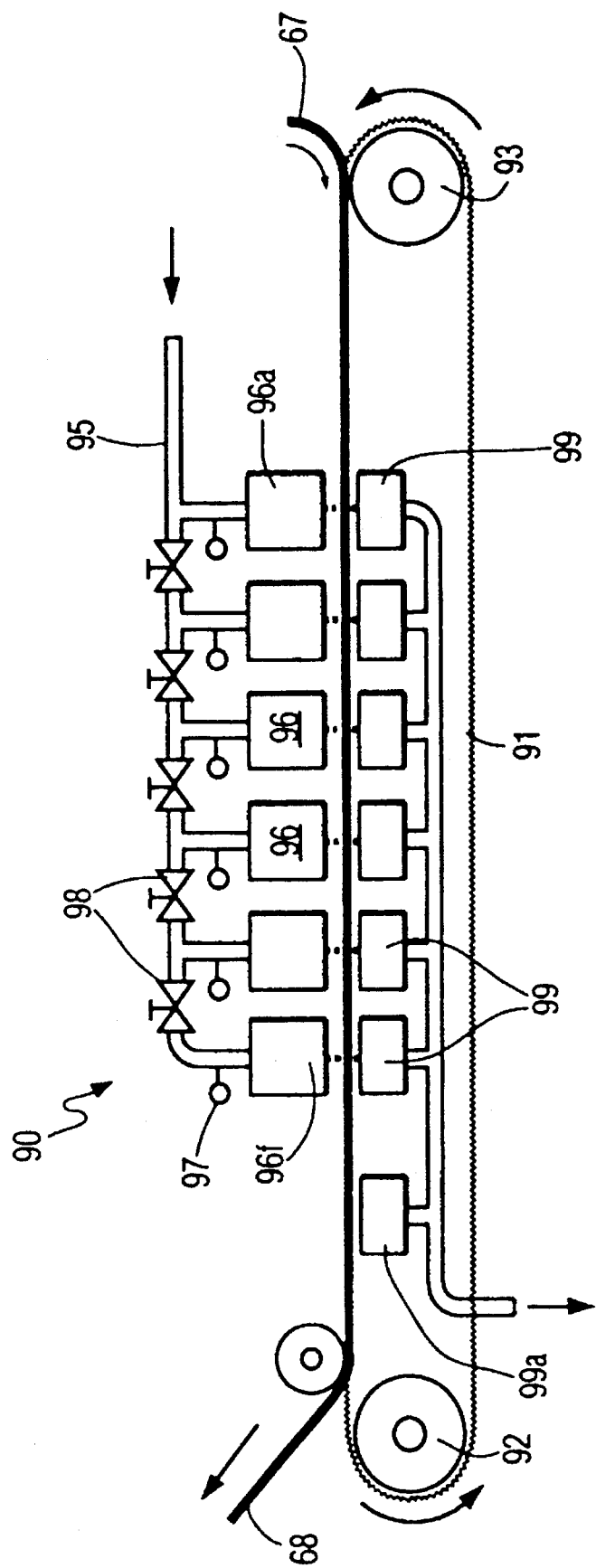
FIG. 21 is a diagrammatic view of another type of apparatus for producing apertured films according to the present invention.

FIG. 21 is a diagrammatic view of an apparatus for continuously producing the apertured films of the present invention. Apparatus 90 comprises a backing member provided in the form of a conveyor belt 91. Conveyor belt 91 is continuously moved in a counterclockwise direction about a pair of spaced apart rollers 92,93 as is well-known. Disposed above conveyor belt 91 is a fluid supply manifold 95 connecting a plurality of lines or groups 96 of orifices. Each group 96 of orifices includes at least one row of very small diameter holes, there being thirty or more of such holes per lineal inch in each row. Manifold 95 is equipped with pressure gauges 97 and control valves 98 for regulating the fluid pressure in each line or group of orifices. Means (not illustrated in the drawings) are provided for supplying water at an elevated temperature to manifold 95. Disposed beneath each orifice line or group is a suction member 99 for removing excess water during processing and to keep the aperturing zone from flooding. The starting film 67 to be formed into the apertured film 68 of the invention is fed to the conveyor belt comprising the backing member. The starting film passes under the group 96 of orifices where it is exposed to the columnar streams of water being ejected from the orifices. The pressure of the water columns being ejected from the individual groups 96 of orifices can be set by pressure control valves 98 to any desired pressure. The pressure of the water supplied to the groups 96 of orifices should be at least about 500 psig and may range up to 1500 psig or even higher. In the process for making apertured films of the present invention, it is preferred that the individual groups 96 of orifices eject water at the same pressure. Though six fluid supplying groups of orifices are shown in FIG. 21, the number of groups of orifices is not critical, but will depend on the thickness of the starting film, the speed of the conveyor belt, the pressures employed, the number of rows of orifices in each group of orifices 96, etc. After passing between the columnar water jets and suction manifold 99, the apertured film 68 passes over an additional suction slot 99a to remove excess processing water therefrom. The conveyor belt comprising the backing member may be made from relatively rigid material and may comprise a plurality of slats. Each slat extends across the width of the conveyor and has a lip on one side and a shoulder on the opposite side so that a shoulder of one slat engages the lip of an adjacent slat to allow for movement between adjacent slats and to allow for these relatively rigid slat members to be employed in the conveyor configuration shown in FIG. 21. Alternatively, the backing member may be a woven screen having high points which support the film and low points into which the film is moved during processing.

Figure 22:
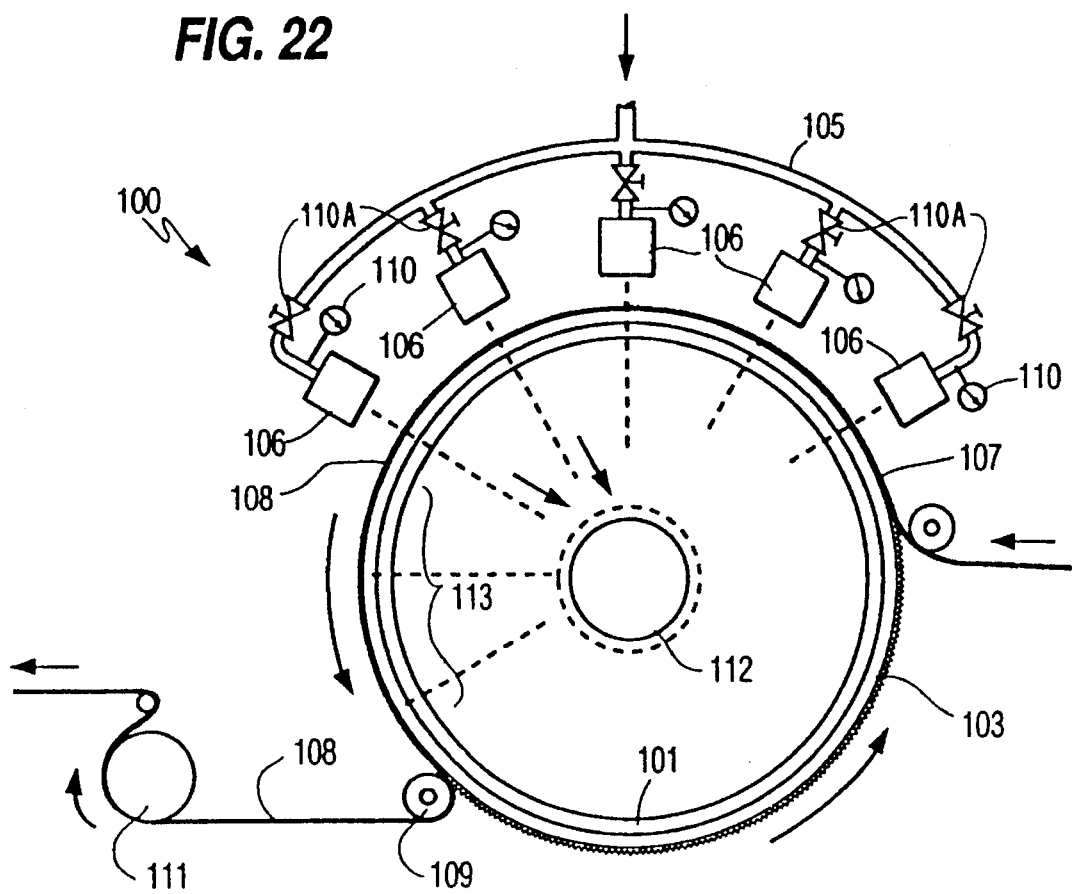
FIG. 22 is a diagrammatic view of a preferred apparatus for producing apertured films according to the present invention.

Referring to FIG. 22, there is shown a preferred apparatus for making apertured films of the present invention. Apparatus 100 comprises a rotatable drum 101. The drum has a honey-comb structure to allow for the passage of fluids therethrough, rotates in a counterclockwise direction and carries a backing member in the form of an elongated cylinder or sleeve 103 placed over its outer surface. Disposed about a portion of the periphery of the drum is a manifold 105 connecting a plurality of orifice strips 106 for applying water to a stretchable thermoplastic starting film 107 carried on the outer surface of sleeve 103. Each orifice strip comprises a row of very fine uniform circular holes. The diameter of these holes should range from approximately 0.005 inch (0.0127 cm) to 0.010 inch (0.0254 cm). There may be as many as 50 or 60 holes per lineal inch or more if desired. Water is directed under pressure through the orifices, forming columnar streams which impinge on the upper surface of the starting film in a contact or aperturing zone below the orifice strips. The pressure of the water supplied to the orifice strips is controlled by pressure control valves 110A, the pressure being indicated by pressure gauges 110. The drum is connected to a sump 112 to which a vacuum may be applied to aid in removing water so as to keep the aperturing zone from flooding. In operation, the starting film 107 is placed on the backing member 103 before the water ejecting orifice strips 106. Film 107 passes underneath the orifice strips where it is formed into the apertured film of the invention.

Example 1

Figure 19:
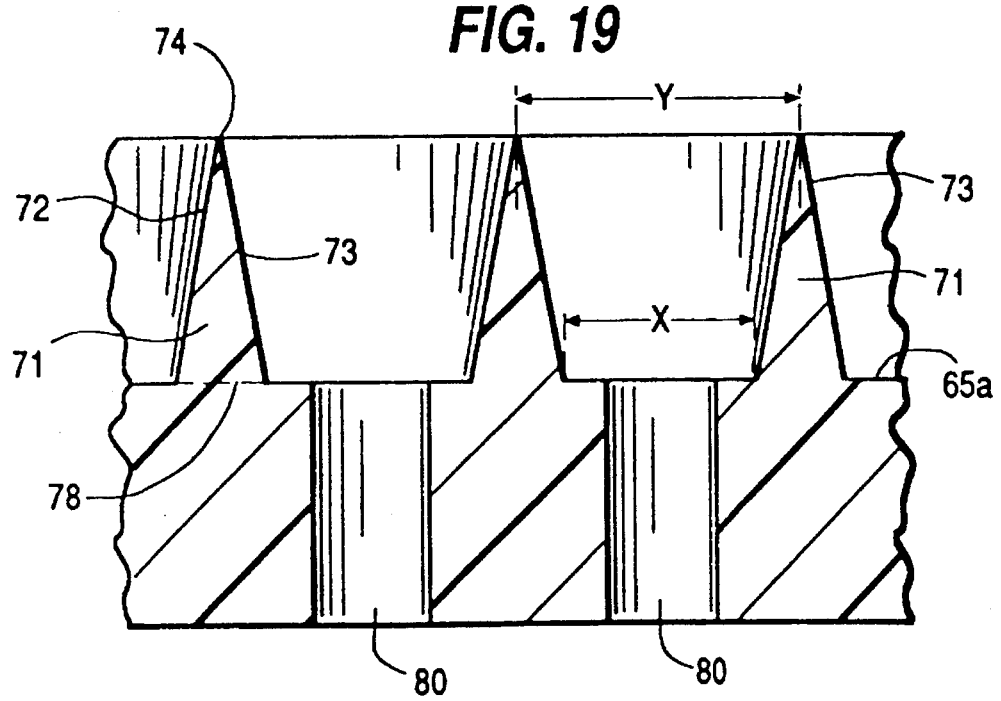
FIG. 19 is a cross-sectional view taken along line 19—19 of FIG. 18.

The apertured plastic film shown in FIGS. 1–5 was made using apparatus 100 of FIG. 22 equipped with the backing member illustrated in FIGS. 17–19. The starting material was a 1.0 mil thick embossed film comprising 50% by weight of linear low density polyethylene and 50% by weight low density polyethylene. The film was obtained from Exxon Corporation under the designation EMB-533. This film had a softening point of 80° C., a melting point of 120 ° C., a specific gravity of 0.91 and a % elongation to break of 460 in the machine direction and 630 in the cross-direction. The film has a MD tensile strength of 3.0 lbs/in and a CD tensile strength of 2.5 lbs/in.

Backing member 103 was provided in the form of a cylindrical sleeve which was placed over support drum 101 as shown in FIG. 22. The outer surface of the backing member had the configuration illustrated generally in FIGS. 17–19. Base 78 measured 0.030 inch (0.076 cm). The height of support elements 71, measured from base 78 to ridge 74, was 0.075 inch (0.191 cm). There were 12 such support elements 71 per inch as measured along reference line A—A of FIG. 18. Support members 71 were aligned circumferentially on the outer surface of the sleeve, i.e. so that reference line B—B shown in FIG. 18 was parallel to the sides of the sleeve.

As shown in FIG. 19, the distance X between adjacent support members 71 at the upper surface 65a of base portion 65 was 0.06 inch (0.152 cm). The distance Y between adjacent support members at their ridges 74 was 0.09 inch (0.229 cm). Apertures 80 were circular and had a diameter of 0.036 inch (0.091 cm). Referring to FIG. 18, apertures 80a, 80b, and 80c were spaced at a center-to-center distance of 0.044 inch (0.112 cm), while aperture 80d was spaced at a center-to-center distance of 0.057 inch (0.145 cm) from adjacent apertures 80c and 80e. This aperture spacing pattern was uniformly employed throughout the backing member.

The cylindrical sleeve comprising backing member 103 was made from Celcon CE-4 acetal copolymer resin available from Hoechst-Celanese. Other materials, such as aluminum, which can be formed into the mentioned cylindrical sleeve may be employed if so desired.

In the process employed for making the apertured film of this Example 1, only three of the five groups 106 of orifices shown in FIG. 22 were used. Each group 106 of orifices had a single row of orifices of diameter 0.005 inch (0.0127 cm), there being 50 such orifices per lineal inch. Each group 106 of orifices was located so that the exits of the orifices were 0.875 inch (2.22 cm) above the ridges 74 of vertical support elements 71. Heated water was supplied to water supply manifold 105 where it was distributed to the three groups 106 of orifices. The water was supplied to the three groups of orifices at a pressure of about 613 psig and at a temperature of 160° F. Starting film 107 was conducted from a let-off roll (not shown in FIG. 22) and led onto the outer surface of the backing member 103 having the sinusoidal-like ridge structure just described. It will be understood that the film was supported on ridges 74 during processing. Support drum 101 carrying the backing member 103 was rotated at 50 ft/min (15.24 m/min) by means of a drive mechanism (not illustrated in the drawings). Water passing through apertures 80 in the backing element 64 and through support drum 101 was removed under suction via sump 112 and was recirculated to the water-supply manifold 105. After passing under the last of the groups 106 of orifices, the now apertured film 108 was led over a dewatering zone 113. Apertured film 108 was then removed from the backing member by stripper roll 109 and passed over the outer surface of a perforated cylinder 111 operating under vacuum to remove any residual processing water prior to further handling or processing.

The apertured film made according to the process of this Example 1 had the structure described earlier herein in connection with FIGS. 1–5 of the drawings.

Example 2

Another apertured film was made using the apparatus and process described in Example 1 except the water was supplied to the three groups 106 of orifices at a pressure of about 600 psig. The starting material was a one mil thick embossed film comprising a blend of low density and linear low density polyethylene. The film was supplied by Edison Plastic of Edison, N.J. as MFST 141. This film has a machine direction tensile strength of 3.3 lbs/in. and an elongation at break of 245%; and a cross machine tensile strength of 2.2 lbs/in. and an elongation at break of 650%. The resulting apertured film was tested and found to have the following properties:

| | |
|---|---|
| Machine direction (MD) tensile strength: | 1.9 lbs |
| Cross direction (CD) tensile strength: | 1.2 lbs |
| % Open Area | 3.0 |
| Mean equivalent hydraulic diameter, mils, of micro-holes | 3.03 |
| Coefficient of Variation (COV) of micro-hole size | 162% |
| Bulk, mils | 23 |
| Strike-through time, seconds | 27 |

MD tensile strengths and CD tensile strengths were determined on 1" wide samples of apertured film using an Instron Testing Machine in accordance with ASTM Test Method D-882.

% open area was determined on a Quantimet Q520 Image Analyzer sold by Cambridge Instruments Ltd.

The open area and EHD of the apertured film were determined by image analysis. Essentially image analysis converts an optical image from a light microscope into an electronic signal suitable for processing. An electronic beam scans the image, line by line. As each line is scanned an output signal changes according to illumination. White areas produce a high voltage and black areas a low voltage. An image of the apertured film is produced and, in that image, the holes in the apertured film are white while the solid areas of thermoplastic material are at various levels of grey. The more dense the solid area, the darker the grey area produced. Each line of the image that is measured is divided into sampling points or pixels. Such analysis is carried out by using a Quantimet Q520 Image Analyzer sold by LEICA/Cambridge Instruments Ltd. The analyzer uses Version 4.0 software with Grey Store Option. The light microscope used is an Olympus SZH Microscope with transmitted light base and plan 0.5X objective. The image is produced with a COHU video camera.

Apertured films are prepared for analysis by sputter coating (30 seconds) in a Polaron II HD sputter coater to render transparent film areas opaque. Samples are mounted on 3 inch×4 inch glass slides using double faced tape (at the ends of the slides) to secure apertured films in position.

A representative piece of each apertured film to be analyzed is placed on the microscope stage and sharply imaged on the video screen at a magnification of 10×. The open area is determined from field measurements of representative areas. The Quantimet program output reports mean value and standard deviation for each sample. The EHD (equivalent hydraulic diameter) of apertures are measured at a magnification of 20×. The Quantimet calculates EHD from the measured area and perimeter of each aperture according to the formula $$EHD = 4 \frac{A}{P}$$

where A=aperture area and P=aperture perimeter.

The Quantimet program output reports the EHD values and standard deviation for each sample.

EHD values can also be determined by the test procedure disclosed in U.S. Pat. No. 4,324,276 mentioned earlier herein. The films produced according to the present invention have apertures, a preponderance of which have EHD values in the range of 0.5 to 25 mils.

Mean value, Standard Deviation (SD) and Coefficient of Variation (COV) are determined using standard statistical methods. COV is determined as follows:

$$COV = \frac{SD}{Mean} \times 100\%$$

Coefficient of Variation of EHD is an indication of the variability of the size of the micro-holes in the apertured film in terms of their Equivalent Hydraulic Diameter. If all micro-holes were of the same EHD, there would be no variation in EHD and the COV of EHD would be 0%. Larger COV's of EHD indicate larger variations in the sizes of the micro-holes in terms of their EHD. As the COV of EHD of apertured films made in accordance with the teachings of the present invention increases, the films increasingly take on the appearance of prior art nonwoven fabric derived from fibrous webs. The films produced according to the present invention have apertures which have a COV of EHD of at least substantially 50%.

Liquid Strike-Through Values were determined as follows. The strike-through test measures the time required for 5 cc of a test liquid to flow through an elliptical opening having a major axis of 1.5 inches (3.81 cm) and a minor axis of 0.75 inch (1.9 cm). The test fluid is a synthetic menstrual fluid designed to emulate the flow characteristics, viscosity, color, and ionic properties of human menstrual fluid. A 0.5 inch (1.27 cm) plexiglass plate with the described elliptical opening was placed on an absorbent pad of the type used in sanitary napkins, said absorbent pad being wrapped in the material to be tested. Five (5) cc of the aforementioned test liquid were then poured through the elliptical opening in the plexiglass plate. The strike-through time in seconds was recorded as the time elapsed between introduction and disappearance of the fluid on the surface of the material being tested.

Example 3

Figure 23:
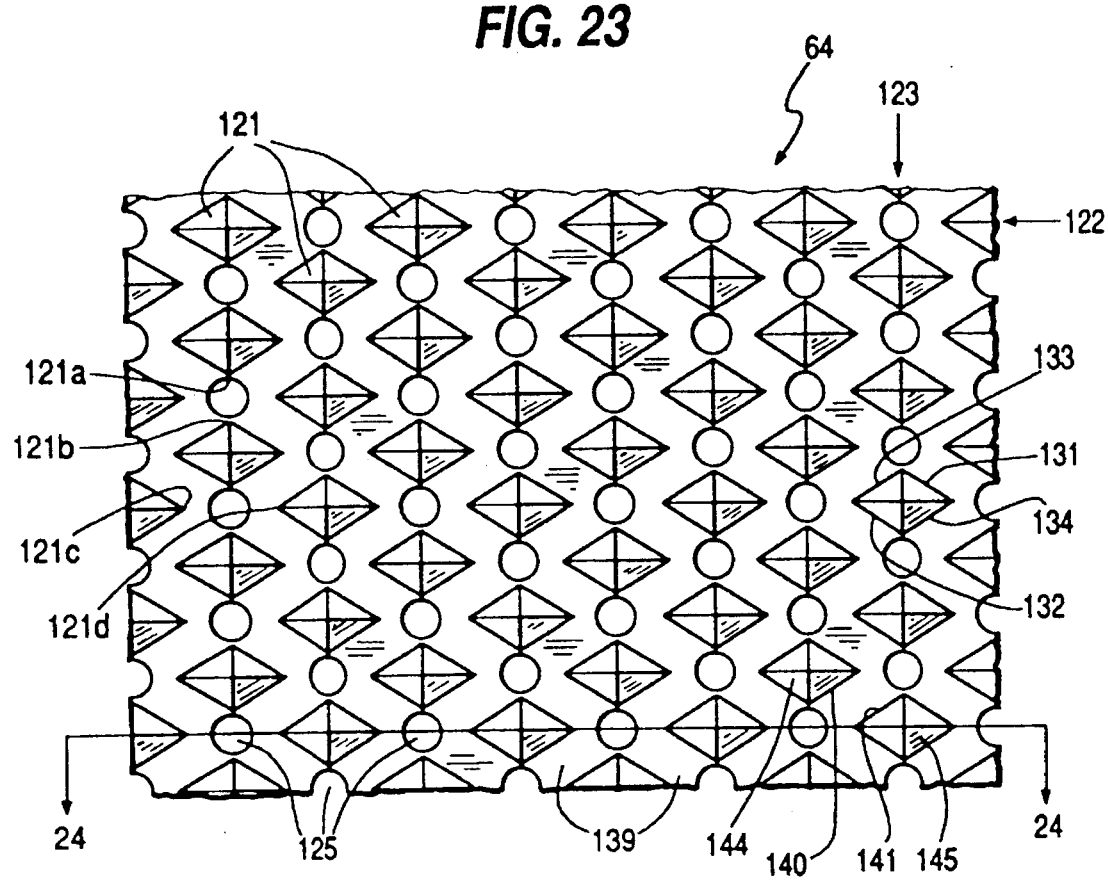
FIG. 23 is a top plan view of the backing member used to produce the apertured film shown in FIGS. 6–10.
Figure 24:
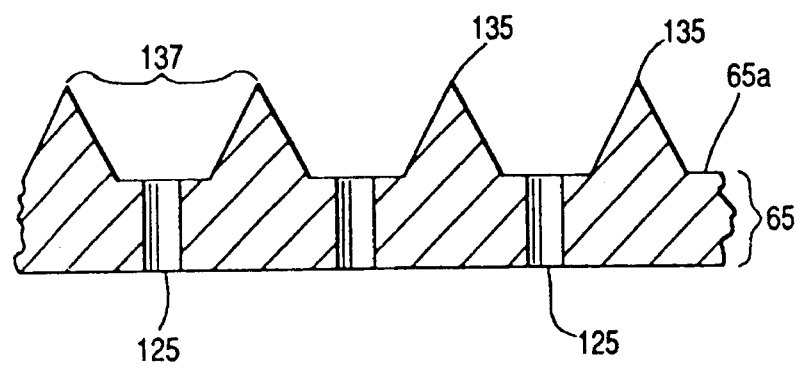
FIG. 24 is a cross-sectional view taken along line 24—24 of FIG. 23.

The apertured plastic film shown in FIGS. 6–10 was made using apparatus 100 of FIG. 22 equipped with backing member 103 shown in FIGS. 23 and 24 of the drawings. In this instance, the backing member 103 comprised a plurality of four-sided pyramids 121 arranged in rows 122 and columns 123. The pyramids extended generally vertically from the upper surface 65a of base portion 65 of backing member 64. The rows of pyramids were disposed horizontally and the columns of pyramids were disposed vertically as viewed in FIG. 23. The rows 122 of pyramids were aligned parallel to the axis of rotation of drum 101. The columns of pyramids were aligned perpendicular to the rows and in a direction parallel to the direction of rotation of drum 101, so that during operation of apparatus 100 the columns of pyramids were aligned in parallel with the machine direction of the apparatus and the machine direction of the thermoplastic film being processed thereon. As can be seen in FIG. 23, the pyramids in any given row were staggered with respect to the pyramids in each of the rows immediately adjacent thereto.

The backing element further comprised a plurality of apertures 125 running through the thickness of base portion 65. Apertures 125 were circular and had a diameter of 0.032 inch (0.081 cm). As seen in FIG. 23, apertures 125 were nearly, but not quite, in contact with each immediately adjacent pyramid 121 in a column 123; in other words, the diameter of apertures 125 was nearly equivalent to the spacing between the apices 121a, 121b of any two adjacent pyramids in a column 123. However, as can be seen in both FIGS. 23 and 24, apertures 125 were spaced a certain distance from each of the immediately adjacent pyramids 121 in a row 122; in other words the diameter of apertures 125 was less than the distance between the apices 121c, 121d of any two adjacent pyramids in a row 122.

The four side edges 131, 132, 133, 134 at the base of pyramids 121 were each 0.037 inch (0.094 cm) in length.

As seen in FIG. 24, the spacing 137 between peaks 135 of two immediately adjacent pyramids in a row 122 was 0.072 inch (0.183 cm). The spacing between peaks 135 of two immediately adjacent pyramids in a column 123 was 0.0415 inch (0.105 cm). Pyramids 121 defined a plurality of intersecting valleys 139 in the backing element, all such valleys being 0.035 inch (0.089 cm) in width as measured perpendicularly from edge 140 of pyramid 144 to edge 141 of adjacent pyramid 145.

The starting film, i.e. Exxon EMB-533, using in Example 1 was also used to make the apertured film of this Example 3. Apparatus 100 (except for the backing element) used for this Example 3 was identical to that used in Example 1. Water was supplied to the three groups of orifices at a pressure of about 1600 psig and at a temperature of 90° F.

Support drum 101 carrying the backing member described with reference to FIGS. 23 and 24 was rotated at 50 ft/min. (15.24 m/min.).

The resulting apertured film had the structure described earlier herein with reference to FIGS. 6–10. The film had the following physical properties:

| | |
|---|---|
| MD tensile strength, lbs./inch | 1.1 |
| CD tensile strength, lbs./inch | 1.3 |
| % open area | 7.02 |
| Bulk, mils | 27 |
| Strike-through time, secs. | 28 |

Figure 6:
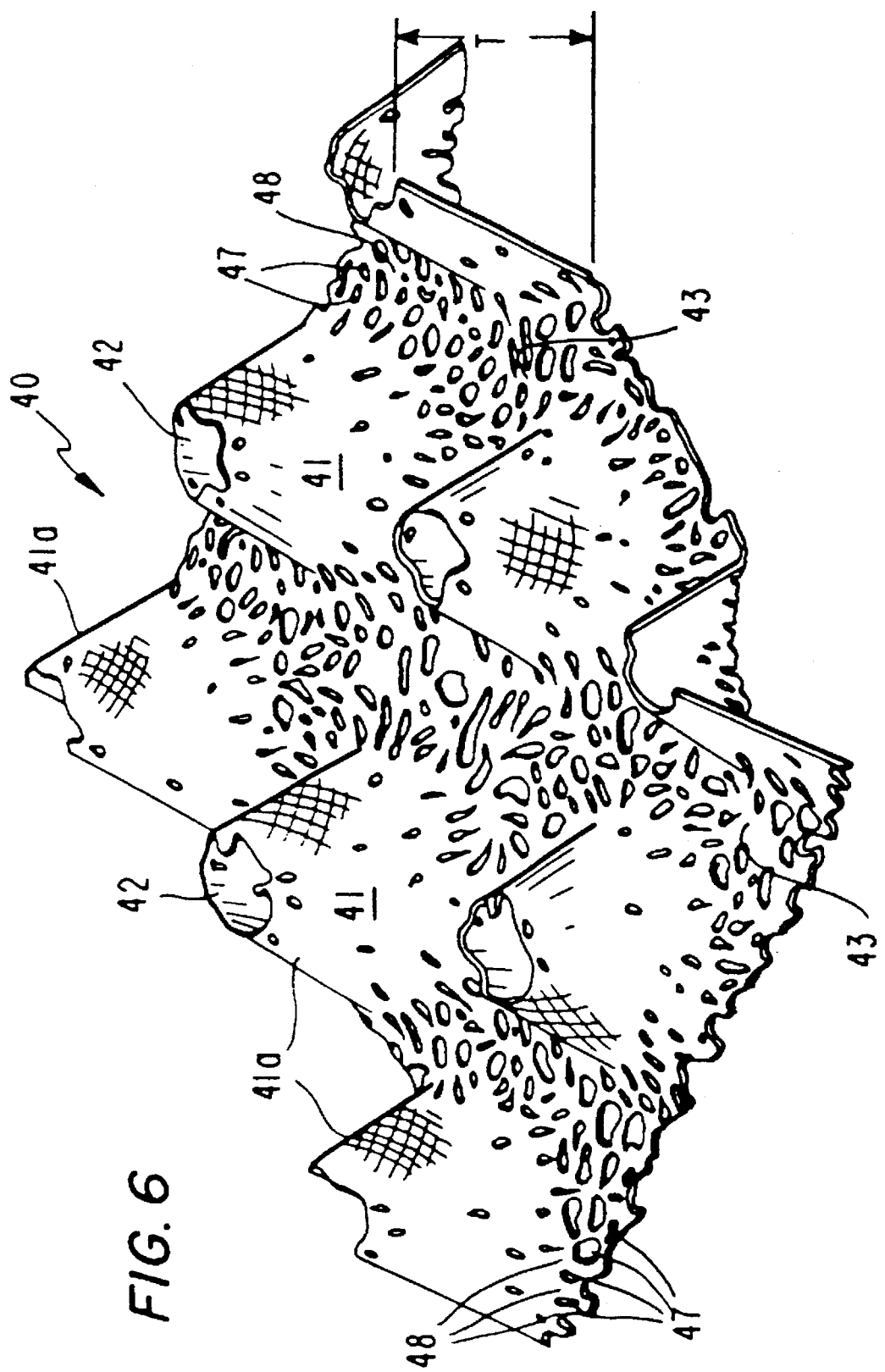
FIG. 6 is a schematic perspective view of the upper surface of a second embodiment of an apertured plastic film according to the present invention.
Figure 11:
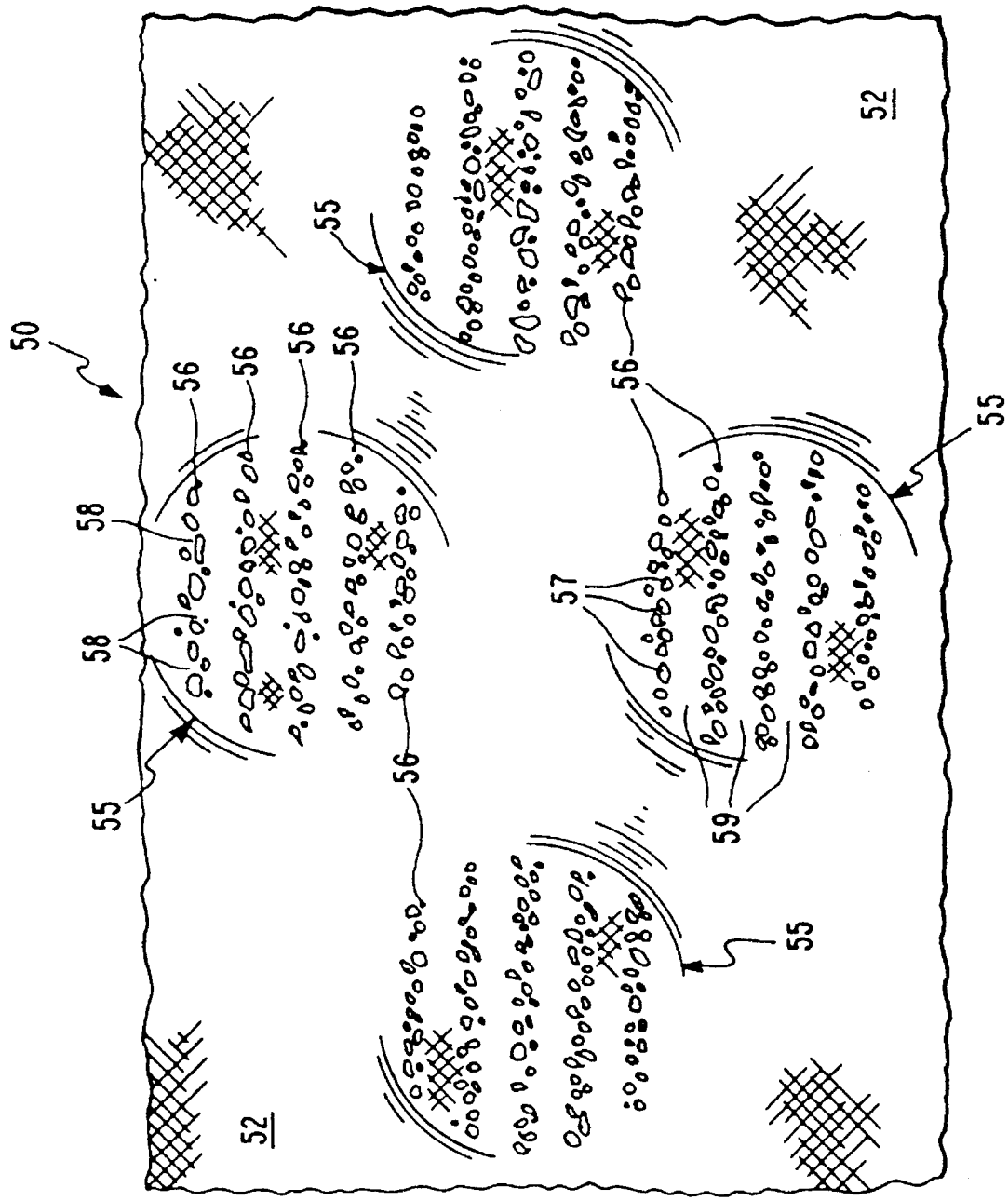
FIG. 11 is a schematic plan view of the upper surface of a third embodiment of an apertured plastic film according to the present invention.
Figure 12:
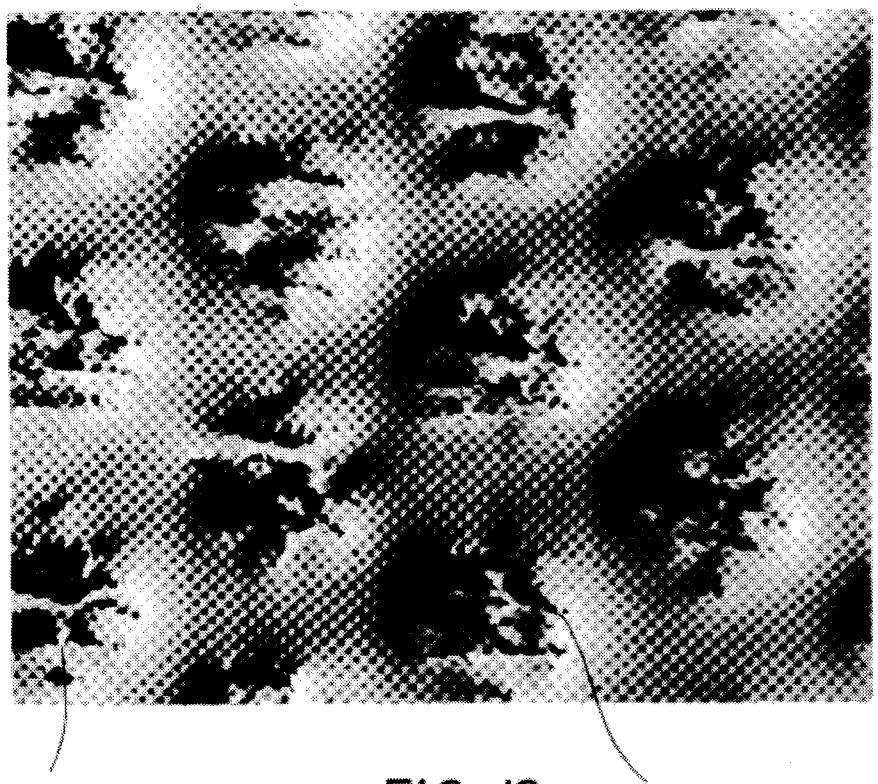
FIG. 12 is a photomicrograph of the upper surface of the apertured film illustrated schematically in FIG. 11 enlarged about 20 times.
Figure 13:
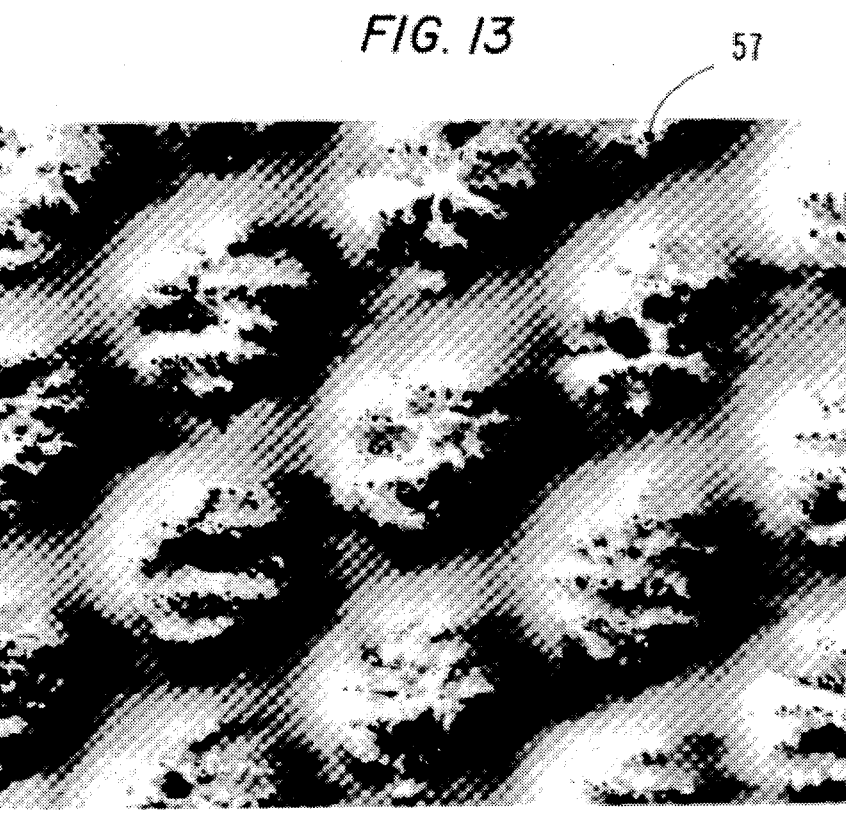
FIG. 13 is a photomicrograph of the lower surface of the apertured film illustrated schematically in FIG. 11 enlarged about 20 times.

Referring to FIG. 6, the mean EHD of micro-holes 47 in the apertured film of this Example 3 was 3.38 mils. The Coefficient of Variation of the EHD of micro-holes 47 was 157%. The apertured film also included a plurality of larger holes 42, these larger holes 42 having been produced when the columnar water jets forced the starting film over the pointed upper surfaces of pyramids 121 of the backing during processing. The mean EHD of larger holes 42 in the apertured film of this Example 3 was 17.32 mils. The wide variation in micro-hole size, as indicated by the COV of EHD of 157%, provided an apertured film whose visual appearance was much more nearly like that of a nonwoven fabric made from a fibrous web. It will be recognized that larger holes 42 in the apertured film under discussion can be eliminated by providing the pyramids with apices which are rounded off, rather than pointed.

The apertured film of Example 3 was found to be particularly useful as facing layer for sanitary napkins.

Example 4

Figure 25:
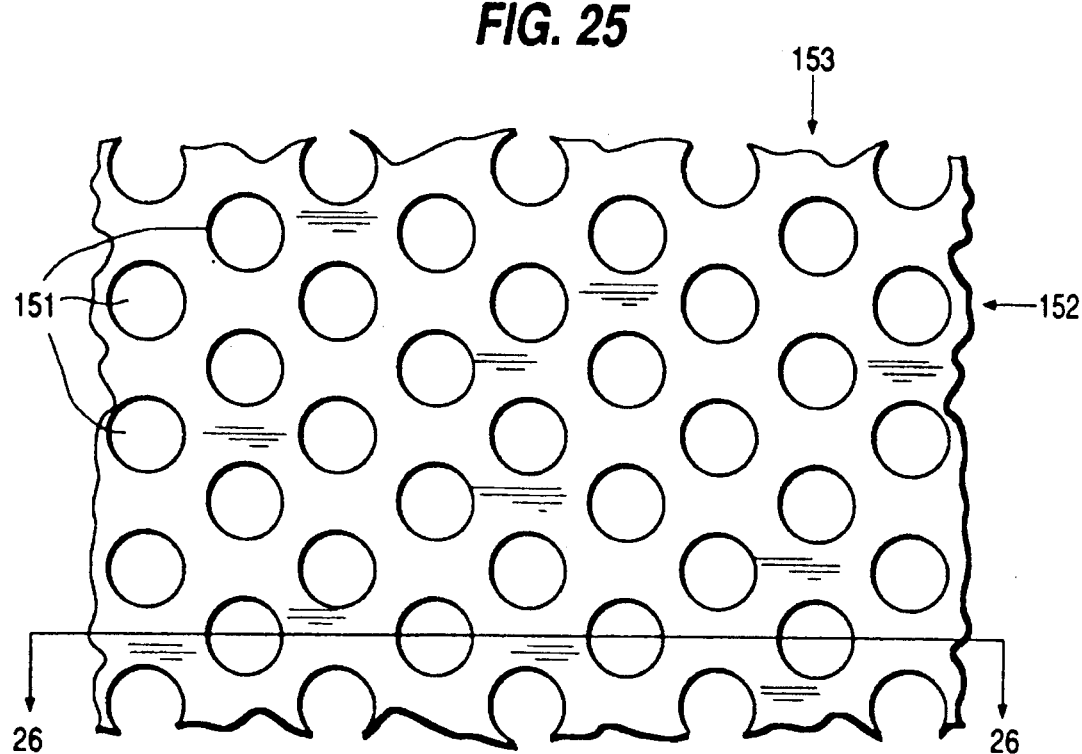
FIG. 25 is a top plan view of the backing member used to produce the apertured film shown in FIGS. 11–15.
Figure 26:
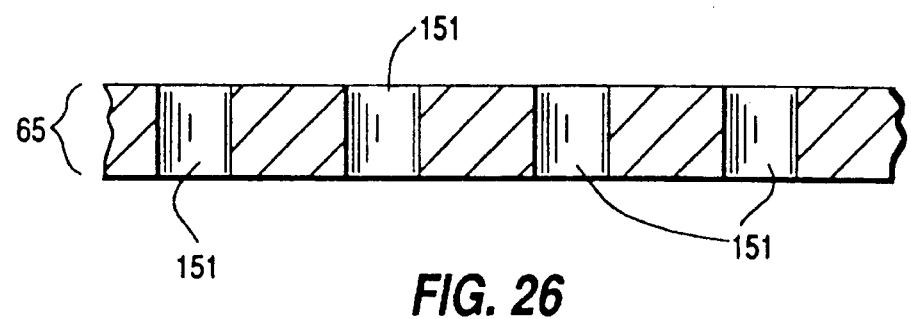
FIG. 26 is a cross-sectional view taken along line 26—26 of FIG. 25.

The apertured plastic film shown in FIGS. 11–15 of the drawings was made on apparatus 100 of FIG. 22 equipped with cylindrical backing member 103 having the configuration shown in FIGS. 25 and 26. Backing member 103 comprised a base portion 65 with a plurality of circular openings 151 arranged in rows 152 and columns 153. Rows 152 were disposed horizontally and columns 153 were disposed vertically as viewed in FIG. 25. Rows 152 were aligned parallel to the axis of rotation of support drum 103. Columns 153 were aligned perpendicularly to rows 152 and parallel to the direction of rotation of drum 101, so that during processing on apparatus 100, columns 153 ran parallel to the machine direction (MD) of the apparatus and the machine direction of the film undergoing processing. As can be seen in FIG. 25, the circular openings in any given row were staggered or offset in the horizontal direction with respect to the circular openings in each of the rows immediately adjacent thereto.

Circular openings 151 had a diameter of about 0.041 inch (0.103 cm). The center-to-center distance between the circular openings in the rows 152 was about 0.067 inch (0.17 cm), while the center-to-center distance between the circular openings in the columns 153 was about 0.041 inch (0.104 cm).

Backing member 103 having the configuration shown in and just described with reference to FIGS. 25 and 26 was provided in the form of a cylindrical sleeve which was placed over support drum 101. The starting film was Exxon EMB-533 used in preceding Examples 1–3. The temperature of the water supplied to the four groups 106 of orifices was 70° F. The water was supplied to the groups of orifices at a pressure of about 800 psig. The water was ejected from the orifices in the form of very fine columnar streams. Support drum 101 was rotated at a speed of about 5 ft/min. (1.5 m/min.). The resulting apertured film has the structure shown in and hereinbefore described with reference to FIGS. 11–16 of the drawings.

The apertured films of Examples 2 and 3 were tested for % open area; Equivalent Hydraulic Diameter (EHD); Coefficient of Variation (COV) of EHD; Range of Hole Size; Coefficient of Variation of Hole Size; Shape Factor; Coefficient of Variation of Shape Factor; and width of the fiber-like elements. % open area, EHD, COF of EHD and size of holes were determined in accordance with the methods described earlier herein.

Shape Factor is an indication of the roundness of a hole or opening in a material being tested. Shape Factor (SF) is defined by the formula:

$$SF = \frac{P^2}{KA}$$

where P is the perimeter of the hole or opening being measured, A is the area of the hole or opening and K is a constant equal to 4Π.

For a hole or opening which is perfectly circular in configuration, the Shape Factor, SF, is unity, i.e. 1. The higher the value of the Shape Factor, the more irregular, i.e. the less circular, is the configuration of the hole or opening. Materials having high Coefficients of Variation (COV) of hole size are much more textile-like in appearance to the viewer, i.e. the materials appear to be much more similar visually to traditional nonwoven fabrics made from fibrous webs and much less visually similar to plastic films having substantially uniform holes or openings. The apertured films of the present invention have COV of shape factor of at least about 25%.

Prior art facing materials were used as controls in the tests being discussed. The first control facing material, Sample C in Table I, was the facing material used on and taken from Kotex brand Super-Maxi sanitary napkins sold commercially by Kimberly-Clark Corporation. The second control facing material, Sample D in Table I, was the facing material used on and taken from Always brand Maxi-Pads sanitary napkins sold commercially by The Procter & Gamble Company. A third control facing material, designated Sample E in Table I, was the facing material used on Sure & Natural brand sanitary napkins sold commercially by Personal Products Company. In Table I, Sample A corresponds to the apertured film made in accordance with Example 2 hereof and Sample B corresponds to the apertured film made in accordance with Example 3 hereof.

The facing material designed Sample C in Table I is a liquid-permeable nonwoven fabric comprising continuous length fibers having substantially uniform diameters of about 1.2 mils, this material being known in the art as a spun-bonded nonwoven fabric.

The facing material designated D in Table I is an apertured plastic material described on the outer package containing the sanitary napkins from which it was taken as "Dri-Weave Covering". This material is evidently made by the process disclosed in U.S. Pat. Nos. 4,342,314 and 4,463,045 which are listed on said outer packaging.

The facing material designated Sample E in Table I was made according to the teaching of U.S. Pat. No. 4,690,679.

TABLE I

| Property | SAMPLE | | | | |
|---|---|---|---|---|---|
| | A | B | C | D | E |
| % Open Area | 3.0 | 10.0 | 17 | 26 | 28 |
| COV of Shape Factor, % | 32 | 29 | 30 | 11 | 17.9 |
| EHD, openings | 95% <25 mils | 90% <25 mils | 95% <25 mils | 75% >25 mils | 95% between 10–18 mils |
| COV of EHD, % | 80 | 87 | 92 | 11 | 7 |
| Hole Size, square mils | 95% between 0.3 and 400 | 95% between 0.3 and 400 | 95% between 0.3 and 400 | 80% between 400 and 750 | 95% between 90 and 400 |
| COV of Hole Size, % | 160 | 190 | 200 | 11 | 24.5 |
| Width of fiber-like elements, mils | 80% between 1 and 5 | 80% between 1 and 5 | 100% 1.2* | 100% between 15 and 30# | 100% between 15 and 35# |

*fiber diameters
width of plastic material between holes

The test results are shown in Table I. It can be seen from these test results that the apertured thermoplastic films of the present invention (Table I, Samples A and B) are very similar to nonwoven fabrics made from fibrous webs (as exemplified by the spunbonded nonwoven fabric Sample C) and are quite dissimilar from the prior art apertured plastic materials exemplified by Samples D and E.

Sanitary napkins were made utilizing the liquid permeable apertured films of Examples 2 hereof and the facing materials described earlier herein and designated C and E in Table I. The napkins were tested for strike-through times, rewet properties and color masking properties.

The sanitary napkins which were tested contained absorbent cores of the type used commercially in Sure & Natural sanitary napkins sold by Personal Products Company and were wrapped with facing materials A, C and D. The facing materials were overlapped and sealed on the lower surface of the test napkins as known in the art, leaving a single layer of facing material on the upper, i.e. body contacting, surface of the napkins.

Strike-through time in seconds for the test sanitary napkins were determined according to the method described earlier herein. After completion of the liquid strike-through test, two plies of 3"×4× filter paper were placed over the area of the sanitary napkin stained by the synthetic menstrual fluid applied during the liquid strike-through test procedure. A four (4) pound roller, 5 inches (12.7 cm) in length and 3.25 inches (8.26 cm) in diameter, was rolled back and forth once over the entire upper surface of the napkin being tested. The amount in grams of synthetic menstrual fluid absorbed by the filter papers was taken as the "rewet value".

Stain-masking properties of various cover materials were determined with the use of a Hunter Color Meter using the following procedure. Sanitary napkins for testing were prepared by wrapping absorbent cores of wood pulp fluff with the cover materials to be tested as described earlier herein. The sanitary napkins to be tested were placed over the specimen part of the Hunter Color Meter and covered with a black calibration glass. Readings were then taken on the L, a and b scales of the meter. This procedure was repeated two more times on different parts of the napkin being tested. The opacity value, OV, of the sample under test was determined by the formula:

$$OV = \frac{M}{N}(100)$$

where M=the digital read-out value on the Hunter Color Meter with the black calibration glass in place; and
where N=the digital read-out value on the Hunter Color Meter with the white calibration glass in place.

The sanitary napkins to be tested are covered with the plexiglass plate used to determine strike-through times. Five (5) cc of the menstrual fluid described earlier herein were poured through the elliptical opening in the plate and allowed to be absorbed by the napkin, simulating the stain which would result from contact by actual menstrual fluid. The intensity of the stain in the stained region of the sanitary napkin was then measured by taking reading on the L, a and b scales of the Hunter Color Meter. Stain Intensity, SI, was determined by the formula:

$$\text{Stain Intensity} = [(L_s-L_{us})^2 + (A_s-A_{us})^2 + (b_s-b_{us})^2]1/2$$

where subscript s=value obtained for stained region and us=value obtained on the unstained control.

Stain Masking Values, SMV, for each covered sanitary napkin was then determined by the formula:

$$SMV = OV - SI$$

where OV is the opacity value and SI is the Stain Intensity.
The test results are reported in Table II.

TABLE 2

| Property | COVER MATERIAL USED ON SANITARY NAPKIN | | |
|---|---|---|---|
| | A | C | D |
| Strike-through time, secs. | 27 | 16 | 16 |
| Rewet value, grams | 0.18 | 0.53 | 0.46 |
| Stain Masking | 70 | 58 | 64 |
| Open Area, % | 3 | 17 | 26 |

Note: Cover material C is a nonwoven fabric which has tortuous paths for passage of fluids. The open area determined by transmitted light measurements may not reflect the total area which allows fluids to pass.
Cover materials A, C and D in Table II correspond to cover materials A, C and D in Table I.

Cover materials A, C and D in Table II correspond to cover materials A, C and D in Table I.

The test results reported in Table II demonstrate that the apertured thermoplastic films of the present invention, as exemplified by the apertured film made according to Example 2 (cover material A, Table II) provide sanitary napkins whose stain-masking properties and rewet values are equal to or better than those of commercially available sanitary napkins utilizing either a spun-bonded nonwoven fabric (i.e. cover material C, Table II) or a plastic apertured cover material (i.e. cover material D, Table II), and whose strike-through times, though somewhat higher than those of existing commercially available products, are nevertheless functionally acceptable. These favorable results are quite surprising in light of the fact that the apertured plastic film of Example 2 hereof significantly lower has an open area than the prior art cover materials C and D.

A Fourier Transform Infra-Red (FTIR) instrument with a microscope attachment was employed to identify draw ratio differences between the fiber-like elements and the polymeric film material portions adjacent those fiber-like elements in the apertured film products of the present invention. It is to be appreciated that in processing the material of the present invention, the starting film is supported on the high points of the backing element and under the influence of the impact of the columnar streams of water the unsupported portions of the starting material are caused to deflect toward and partially into the depressed regions or valleys of the backing element.

This deflection or stretching continues until the starting film breaks into the micro-holes and fiber-like elements characteristic of the apertured films of the invention. The stretching or drawing is localized in that most of the stretching or drawing occurs in those portions of the starting film which become the fiber-like elements. The purpose of this test is to determine the difference in the stretch which has occurred in the fiber-like elements and in the polymeric material adjacent the areas of fiber-like elements.

These determinations were made using a dual bench FTIR spectrometer (Model 1800 FTIR, Perkin-Elmer Corp., Norwalk, Conn.) equipped with a research grade IR microscope (IRPLAN infrared microscope, Spectra Tech, Stamford, Conn.) operated in the transmittance mode. IR spectra were obtained using a medium band, 1 mm$^2$, mercury-cadmium-telluride (MCT) detector, and a 15X cassigrain (IR) objective lens. The spectra were scanned at a resolution of 2 cm$^{-1}$ between 4000 and 600 cm$^{-1}$. The data interval used was limited to 1 (sec./spectrum) for a resolution of 2 cm$^{-1}$. The operational mode parameter for the background and the apertured film samples examined were the same except for the Jacquinot stop which was 1 for the background and 4 for the processed samples. The normal Hays-Ganzel apodization function was used in all cases. All specimens were scanned 200 times with the necessary apertures in place. One collection of background scans were used to ratio the subsequent test sample spectra. The background spectrum was acquired using a 1 mm aperture in the condenser, a 1 μm pinhold in the sample tray, and a 1.5 mm aperture in the upper optical module. The sample spectra was acquired using redundant aperturing above and below the sample so as to pinpoint the specific area of interest in the samples to be examined.

A draw ratio calibration curve was developed by mechanically deforming the starting polymeric film material measured amounts of elongation from 0 to 500% in 100% increments and obtaining FTIR spectra for each sample.

Spectra were then obtained from fiber-like elements in the apertured film material and from the areas immediately adjacent those fiber-like elements. These spectra were compared to the spectra of the calibration curve and the degree of elongation of the fiber-like elements was determined therefrom. It was found that the fiber-like elements of the apertured film of the invention had been drawn at least 100% as compared to adjacent regions of starting film which had not undergone aperturing during processing. A major portion of the fiber-like elements were found to have been drawn from about 200% to about 250% compared to adjacent regions of starting film which had not undergone aperturing during processing.

As indicated earlier herein, apertured films of the present invention may be used as facing materials for absorbent products such as disposable diapers, sanitary napkins, wound dressings, incontinent devices and the like.

When used as covering materials for sanitary napkins, it is preferred that the micro-holes of the apertured thermoplastic films of the present invention be sufficient in number to provide an open area ranging from about 1–15%, with the number of larger-sized holes (such as those numbered 42 in FIG. 6 of the drawings) preferably being minimized. It is preferred that at least fifty percent (50%) of the micro-holes comprising the film have EHD's ranging between 0.5 and 25 mils. The COV of EHD of the micro-holes is preferably at least 50%. Preferably, at least seventy-five percent (75%) of the micro-holes have areas less than 400 square mils and the Coefficient of Variation of micro-hole area should be at least 100%.

Figure 27:
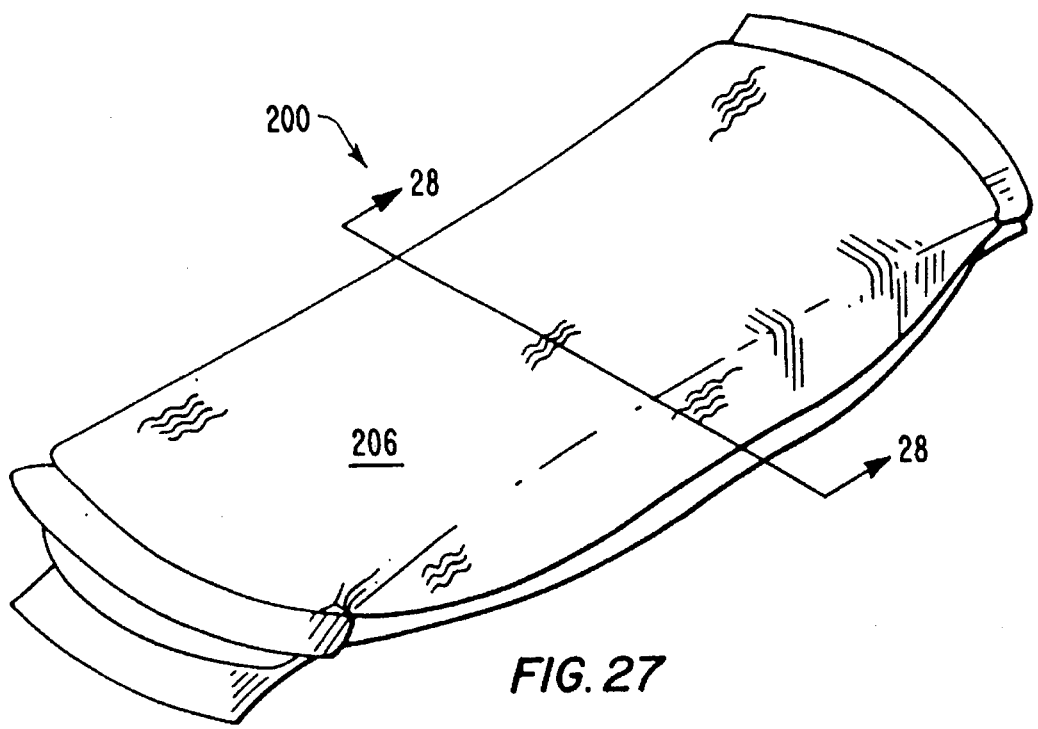
FIG. 27 is a perspective view of a sanitary napkin comprising an apertured film according to the present invention.
Figure 28:
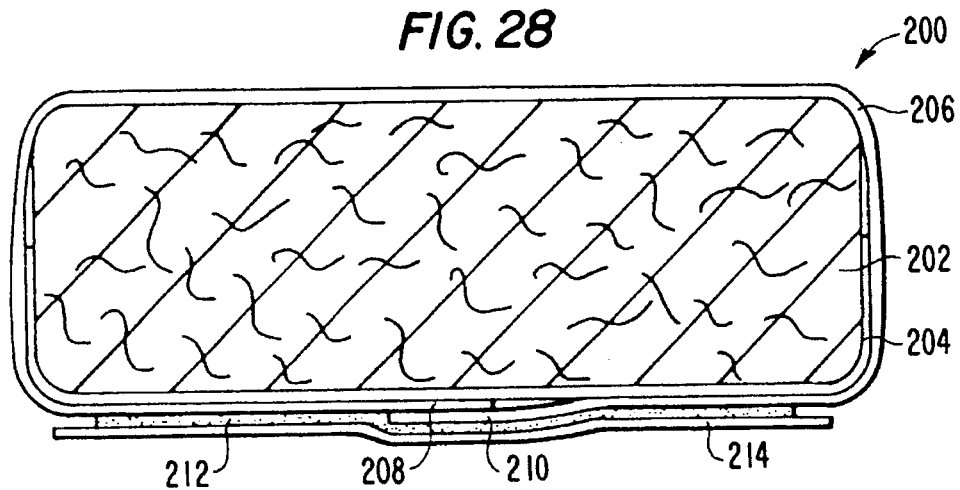
FIG. 28 is a view, partially in section, taken along line 28—28 of FIG. 27.

Referring to FIGS. 27 and 28, there is shown a sanitary napkin 200 comprising an absorbent core 202 of wood pulp fibers, a thin, fluid-impermeable barrier film 204 and a covering material 206 which may be any of the apertured films of the invention. Preferably, the covering material has the structure shown and described herein with reference to FIGS. 1–5 and Example 2. Barrier film 204, which may comprise, e.g. a thin film of polyethylene, contacts the lower surface of absorbent core 202 and runs part way up the longitudinal sides of the absorbent core. Covering material 206 has a length somewhat longer than the length of the absorbent core and is wrapped around the absorbent core and barrier film as shown in FIG. 28. The longitudinal edges of the cover material are overlapped and sealed together on the lower surface of the napkin in the usual manner. In the embodiment illustrated, the cover material is sealed to itself at the ends 208,210 of the sanitary napkin. As illustrated in FIG. 28, sanitary napkin 200 has a layer of adhesive 212 for adhering the napkin to the undergarment of the user. Adhesive 212 is protected prior to use by a removable release strip 214.

Variations can be made in the structure of the backing element described-herein. For example, the pyramids shown in FIG. 23 may have 3, 5 or more sides. The backing element could also have upstanding support elements in the form of cones, square bosses, etc.

We claim:

1. A method for forming an apertured film comprising a stretchable thermoplastic polymeric material having a plurality of micro-holes therein, said micro-holes being defined by a network of fibrils formed from said thermoplastic polymeric material, said method comprising:

a) providing a starting film comprising said stretchable thermoplastic polymeric material and having an upper surface and a lower surface;

b) providing a backing member comprising localized support regions for supporting said starting film, recessed zones into which the film may be deformed by the application thereto of fluid forces; and means for allowing said applied fluid to be transported away from said backing member;

c) supporting said starting film on said backing member with portions of the lower surface of said film being in contact with the support regions of said backing member and with the upper surface of said film facing away from said backing member;

d) providing a manifold adjacent to the starting film on said backing member, said manifold having a plurality of holes therein having areas ranging from about 7.07×10$^{-6}$ square inches to about 78.5×10$^{-6}$ square inches;

e) directing a fluid through said manifold holes in the form of columnar streams against the upper surface of said starting film in a zone of contact and at a pressure sufficient to urge the unsupported portions of said starting film between said supported portions downwardly at least partially into said recessed zones and to cause the formation of said micro-holes and fibrils;

f) moving said film from said contact zone; and g) removing said now-apertured film from said backing member.

2. A method according to claim 1 wherein said fluid is under pressure ranging from about 500 psig to about 1600 psig.

3. A method according to claim 1 wherein said fluid is water which is directed at the upper surface of said film at a temperature of at least about 90° F.

4. A method according to claim 3 wherein said water is under pressure ranging from about 500 psig to about 1600 psig.

5. A method according to claim 1 wherein said step of moving said film from said contact zone is performed before the unsupported portions of said film are urged completely into said recessed zones.

6. A method according to claim 1 wherein the film supporting step is performed by supporting said film on pointed localized support regions, and the fluid directed against said upper surface of said starting film cooperates with said localized support regions to form openings in said starting film larger than said micro-holes.

7. A method according to claim 1 wherein said starting film is embossed and at least one of the surfaces of said starting film is corona-discharge treated.

8. A method according to claim 7 wherein said starting film is modified by a surface active agent.

9. A method according to claim 1 wherein the film supporting step is performed by supporting said film on sinusoidally shaped localized support regions, and said fluid directed against said upper surface of the starting film cooperates with said sinusoidally shaped localized support regions to form sinusoidally shaped ridges in said apertured film.

10. A method according to claim 1 wherein the step of directing said fluid results in the formation of holes in said film that are larger in size than said micro holes.

11. A method according to claim 10 wherein said film is modified by a surface active agent.

12. A method according to claim 11 wherein said starting film is embossed, and at least one of the surfaces of said starting film is corona-discharge treated.

13. A method according to claim 1 wherein said manifold is positioned with the exits of the holes therein spaced 0.875 inch from the support regions of the backing member.

14. A method according to claim 1 wherein said holes are circular.

* * * * *